(12) United States Patent
Mizutani et al.

(10) Patent No.: US 7,307,197 B2
(45) Date of Patent: Dec. 11, 2007

(54) INTERLABIAL PAD HAVING A LABIAL-FOLLOWING LAYER

(75) Inventors: Satoshi Mizutani, Kagawa (JP); Koichi Yamaki, Kagawa (JP); Yuki Noda, Kagawa (JP); Megumi Tokumoto, Kagawa (JP); Akane Sakai, Kagawa (JP)

(73) Assignee: Uni-Charm Corporation, Ehime-Ken (JP)

( * ) Notice: Subject to any disclaimer, the term of this patent is extended or adjusted under 35 U.S.C. 154(b) by 0 days.

(21) Appl. No.: 11/074,325

(22) Filed: Mar. 3, 2005

(65) Prior Publication Data
US 2005/0215969 A1 Sep. 29, 2005

Related U.S. Application Data

(63) Continuation of application No. PCT/JP03/10767, filed on Aug. 26, 2003.

(30) Foreign Application Priority Data
Sep. 12, 2002 (JP) .............................. 2002-267136

(51) Int. Cl.
*A61F 13/15* (2006.01)
*A61F 13/20* (2006.01)
(52) U.S. Cl. ................. 604/367; 604/378; 604/385.17; 604/904
(58) Field of Classification Search .......... 604/385.17, 604/378–382, 379, 385.18, 904, 367
See application file for complete search history.

(56) References Cited

U.S. PATENT DOCUMENTS 2,331,355 A * 10/1943 Strongson .................. 604/365
2,787,271 A * 4/1957 Clark ......................... 604/375
4,631,062 A * 12/1986 Lassen et al. ........... 604/385.02
4,804,380 A * 2/1989 Lassen et al. ........... 604/385.17
5,591,150 A * 1/1997 Olsen et al. ............. 604/385.23
5,599,335 A * 2/1997 Goldman et al. ........... 604/368
5,672,165 A * 9/1997 Belecky et al. ............. 604/383
5,968,026 A * 10/1999 Osborn et al. .............. 604/378
6,183,456 B1 * 2/2001 Brown et al. .......... 604/385.01
6,316,688 B1 * 11/2001 Hammons et al. .......... 604/378
6,319,238 B1 * 11/2001 Sartorio et al. ............. 604/330

(Continued)

FOREIGN PATENT DOCUMENTS

JP 2000-225138 A1 8/2000

(Continued)

*Primary Examiner*—Michele Kidwell
(74) *Attorney, Agent, or Firm*—Darby & Darby

(57) ABSTRACT

In an inter-labia pad comprising an absorbing body for absorbing bodily fluid and a cover material for covering the absorbing body, the cover material has a human body-side face that faces the labia of a wearer and an absorbing body-side face that faces the absorbing body. The absorbing body includes a labia-following layer and a bodily liquid-storing layer. The labia-following layer, together with the cover material, deforms in accordance with the shape of the wearer's labia, and the bodily liquid storing-layer is in contact with the labia-following layer so that bodily liquid can move from the labia-following layer to the liquid-storing layer. The pad can be reliably fit to subtle shapes of the wearer's urethral opening, private parts, etc.; therefore the pad provides excellent appearance, and prevents bodily liquid from leaking without giving the wearer sense of discomfort.

15 Claims, 11 Drawing Sheets

U.S. PATENT DOCUMENTS

| | | | |
|---|---|---|---|
| 6,575,948 B1 * | 6/2003 | Kashiwagi et al. | 604/385.101 |
| 2002/0026169 A1 * | 2/2002 | Takai et al. | 604/378 |
| 2004/0167491 A1 * | 8/2004 | Mizutani | 604/385.17 |
| 2004/0199134 A1 * | 10/2004 | Mizutani et al. | 604/367 |

FOREIGN PATENT DOCUMENTS

| | | |
|---|---|---|
| JP | 2001-000474 A1 | 1/2001 |
| JP | 2001-506168 A1 | 5/2001 |
| JP | 2001-507597 A1 | 6/2001 |
| JP | 2001-523524 A1 | 11/2001 |
| JP | 2002-505606 A1 | 2/2002 |
| JP | 2002-065735 A1 | 3/2002 |
| JP | 2002-512851 A1 | 5/2002 |
| WO | WO 0040197 A1 * | 7/2000 |

* cited by examiner

INTERLABIAL PAD HAVING A LABIAL-FOLLOWING LAYER

CROSS-REFERENCE TO RELATED APPLICATIONS

This application is a Continuation of International Application No. PCT/JP2003/10767 filed Aug. 26, 2003, which application published in Japanese on Mar. 25, 2004 as WO 2004/024050 A1 under PCT Article 21 (2). The International Application PCT/JP2003/10767 is based upon and claims the benefit of priority from Japanese Patent application No. 2002-267136 filed on Sep. 12, 2002, the entire contents of which is incorporated herein by reference.

FIELD OF THE INVENTION

The present invention relates to an interlabial pad capable of being appropriately worn between labia, and relates to the interlabial pad which retains appropriate wearing without falling out even when the pad's condition becomes wet by absorbing body fluid such as menstrual blood.

RELATED ART

Conventionally, sanitary napkins and tampons have been generally used as feminine menstrual sanitary items. Here, for sanitary napkins, numerous efforts have been made in order to prevent leakage of menstrual blood from a gap, which occurs due to poor adhesiveness in the vicinity of the ostium vaginae. Also, for tampons, a foreign feeling and discomfort while wearing, and wearing difficulty inside the vagina occur due to their attributes, and thus numerous efforts have been made to eliminate these.

Under such circumstances, recently, a sanitary item referred to as an interlabial pad has been known as a sanitary item, which is located at an intermediate position between the sanitary napkin and tampon.

This interlabial pad is worn by placing it between labia, and has characteristics in that it is unlikely to cause leakage of menstrual blood because adhesiveness to the body is higher than that of sanitary napkins and in that psychological resistance to wearing it is lower than a tampon, which is inserted inside the vagina.

For example, an interlabial device or pad having a characteristic absorbent body has been disclosed in Unexamined Japanese Patent Publication No. 2002-505606. This absorbent body comprises an acquisition member having first pores comprising a first pore volume distribution, and a storage member that communicates by fluid with said acquisition member. Said acquisition member is characterized in that, in said first pore volume distribution, at least 75% of said first pores have a capillary radius of 20 μm or more, and has second pores where the average capillary radius is set to be smaller than the average capillary radius of the first pores. This enables to directly acquire menstrual blood discharged from the ostium vaginae because the acquisition member and vestibule of the wearer can contact to be opposed, and enables to circulate the acquired menstrual blood to the storage member where the average capillary radius is set to be small by a capillary phenomenon. Thus, menstrual blood is not stored at the acquisition member, and it is possible to directly acquire menstrual blood at the acquisition member in no time even when menstrual blood is discharged again. Also, it is considered that gradually discharged menstrual blood can be sufficiently acquired and leakage of menstrual blood is reduced.

In this conventional example, a main body part of the absorbent body is constituted so that the storage member with a small average capillary radius, i.e., high density is positioned at the outside so as to sandwich from the sides of the acquisition member which extends downward along a longitudinal direction centerline. Also, this acquisition member was designed to be smaller in density than the storage member. Therefore, it is unlikely to follow shape changes of the labia, which easily changes in connection with behavioral changes of the wearer and outside pressure of garments.

For example, when outside pressure is given to the labia from downward to upward in a vertical direction (from the front of the labia toward the vestibule) by being pressed by undergarments or an action where the wearer sits on a chair, shapes of the labial inner wall change because the labia are inflected in a right-and-left direction to be collapsed. Furthermore, when behavioral changes that such outside pressure is released, for example, when a standing posture is assumed, the labial inner wall returns to a substantially-flat shape. This way, the shape of a labial inner wall is deformed by outside pressure according to the behavioral changes of the wearer, however, it is considered that in the above conventional art, the storage member where the density is set to be high is positioned in the vicinity of the labial inner wall, thus it is difficult that the storage member follows and is deforms, and a space between the labial inner wall and the interlabial pad easily occurs. Thus, there are possibilities that the interlabial pad falls due to reductions in the contact area of the interlabial device or pad with the labia and that a rigid feeling, i.e., a foreign feeling of the storage matter given to the wearer occurs.

Furthermore, general discharge pathways of menstrual blood are broadly classified into (1) a pathway of being retained in the vicinity of the ostium vaginae; (2) a pathway which flows in the cross direction along the vestibule; and (3) a pathway which flows in a downward direction along the labial inner wall. (1) and (2) are discharge pathways where a discharge flow rate is relatively slow and a small amount thereof is gradually discharged. However, (3) is believed to be a discharge pathway with a rapid discharge flow rate and at a large amount since menstrual blood retained in a large amount in the uterus, etc., is discharged at a momentary behavioral change of a wearer. In the conventional art described above, in discharge pathways of (1) and (2), discharged menstrual blood is acquired in the vicinity of the ostium vaginae by the acquisition member to circulate it to the storage member, thereby re-discharged menstrual blood can be acquired. However, in the discharge pathway of (3), menstrual blood is easily retained at an interface between the labial inner wall and the surface of the interlabial pad by accumulating menstrual blood at a position close to the labial inner wall, contact force of the labial inner wall with the interlabial pad is reduced due to fluidity of menstrual blood, and thus the possibility that the interlabial pad falls is increased.

SUMMARY OF THE INVENTION

The present invention provides an interlabial pad, wherein a foreign feeling to the wearer is reduced by enabling it to be easily deformed following behavioral changes in the labial inner wall, where leakage of menstrual blood is prevented by reliably acquiring and storing menstrual blood even in a discharge pathway of menstrual blood discharged downward along the labial inner wall at a rapid flow rate and at a large amount, and further, discharged menstrual blood is made difficult to be retained on the surface of the interlabial pad by making menstrual blood accumulate from a garment side of an absorbent body, thereby falling off of the interlabial pad can be reduced.

More specifically, the present invention provides the interlabial pad characterized by being a shape capable of being placed between a woman's labia comfortably, and by comprising an absorbent body for absorbs body fluid and a covering material for covering the absorbent body, and in that the absorbent body is including a labial following layer positioned to be close to the labia and the body fluid storage layer positioned in close proximity to make menstrual blood pass from the labial following layer. Also, this interlabial pad is characterized in that it can easily deform while wearing since the labial following layer is more easily compressed than the body fluid storage layer, and an apparent density of the labial following layer is lower than that of the body fluid storage layer.

This way, the labial following layer capable of being more easily compressed and deformed than the body fluid storage layer is positioned in the vicinity of the labial inner wall. Thus, even when the labia are inflected right-and-left directions with respect to an axis of the vertical direction, and the labial inner wall makes a convexo-concave shape and is deformed, the labial following layer can be easily compressed and deformed to the behavioral changes of the labial inner wall. Furthermore, since at least a part of the body fluid storage layer facing the labial inner wall is covered with the labial following layer, a rigid feeling of the body fluid storage layer is reduced by the labial following layer and thus a foreign feeling to the wearer can be reduced.

Also, the labial following layer where the density is set to be low is positioned at a location closer to the labial inner wall, and at a reverse side, the body fluid storage layer where the density is set to be high is positioned. Since the labial following layer is easily deformed and opposed in response to morphological changes of the vestibule and the labial inner wall, it can acquire menstrual blood with respect to the discharge pathway at a rapid flow rate and at a large amount which flows downward along the labial inner wall. The menstrual blood acquired at the labial following layer can be accumulated at said body fluid storage layer by a capillary phenomenon. Thus, it is possible to make menstrual blood difficult to be retained on the surface of the interlabial pad. Therefore, it is possible to prevent falling off of the interlabial pad due to fluidity of menstrual blood.

In the absorbent body of the sanitary napkin comprising at least a two-layer structure, by setting the density in the lower layer part higher than that in the upper layer part, menstrual blood acquired in the upper layer part is transferred to the lower layer part and stored therein by a capillary phenomenon, thereby it becomes possible to acquire menstrual blood again in the upper layer part even when menstrual blood is discharged again, and further, it is possible to reduce the possibility of menstrual blood leakage by preventing flowback of menstrual blood due to a change in body pressure.

However, in the sanitary napkin, adhesiveness to the pudendum was increased by making the upper layer part convex and by covering the upper layer part with the lower layer part in order to intimately adhere to a woman's labia which are concave. Thus, a larger size of the lower layer part than the upper layer part is required, and it is a requirement that a lateral dimension is larger at the lower layer part than the upper layer part.

In the interlabial pad of the present invention, a face of the body fluid storage (e.g., lower layer) which is close to the labial inner wall is covered with the labial following layer (e.g., upper layer), therefore, a foreign feeling to the wearer is reduced, as well as adhesiveness of the labial following layer to the labial inner wall and further adhesiveness to the pudendum can be increased, and thus menstrual blood leakage can be prevented. The depth of a woman's labia varies depending on individual differences and changes of body position, however, even when interlabial depth changes occur, gap due to the thickness of the body fluid storage layer is not caused by making the labial following layer larger than the body fluid storage layer in the lateral dimension of the absorbent body, therefore, the labial following layer can retain adhesiveness to the labial inner wall and further to the pudendum, and thus it becomes possible to prevent menstrual blood leakage.

More specifically, the present invention provides the following.

(1) An interlabial pad comprising: an absorbent body for absorbing the body fluid; and a covering material for covering said absorbent body, wherein the covering material has a body side face facing to labia of a wearer and an absorbent body side face facing said absorbent body; said absorbent body comprises a labial following layer and a body fluid storage layer; at least a part of said labial following layer is positioned between said covering material and said body fluid storage layer, and the labial following layer is capable of deforming together with said covering material in accordance with a labia shape of the wearer; said body fluid storage layer is in contact with said labial following layer so as to move the body fluid from said labial following layer to said body fluid storage layer; and said labial following layer is more flexible than said body fluid storage layer.

Here, "the covering material" can be a component that forms an outer covering of a part of the interlabial pad of the present invention. Therefore, it can contact directly or indirectly with the labial inner wall of the wearer. "Body side facing the labia of the wearer" can include the face where the covering material can contact with the labial inner wall of the wearer. This "absorbent body side facing the absorbent body" can include the face of a so-called backside of the body side of the covering material. This covering material can include a sheet member that extends two-dimensionally.

At least a part of "labial following layer" is positioned between the coating material and the body fluid storage layer, however, the outer covering of the labial following layer may serve as the covering material. Therefore, a state can be included where the labial following layer is directly in contact with the labial inner wall. The labial following layer contacts directly or indirectly with the labial inner wall without being in contact with the body fluid storage layer, and can make the shape thereof follow according to the shape of the inner wall. At such a time, it follows along with the covering material, and this covering material can include the outer covering of the labial following layer itself. The labial following layer is preferably deformed more easily than the body fluid storage layer in a dried state and/or a wet state where the body fluid (or menstrual blood) is absorbed and it is particularly preferable that compression is easy when the compression deformation is required. For example, it is preferable that compression rigidity (LC) (Katoh Tec "KES Compression Property") is a lower value in the labial following layer than in the body fluid storage layer regardless of the dried and wet states. Here "the body fluid" is a broad concept including menstrual blood. Also, in the absorbent body, occurrence of gap between the labial inner wall and the interlabial pad is inhibited by making the lateral dimension of the labial following layer larger than that of the body fluid storage layer. However, when the lateral dimension is made too large, there are some unfavorable cases in terms of the balance between the repulsion force and the labial interleaving force.

"The body fluid storage layer" is higher in density than the labial following layer and easily gives a rigid feeling, and thus, it is possible to prevent from giving a rigid feeling to the labial inner wall by positioning the labial following layer intermediately. The body fluid storage layer is preferably in a porous state, and, for example, can comprise a layer including a fibrous assembly, however, it is not limited thereto. For example, the body fluid storage layer may include a continuous matrix having numerous open pores. Capillary radius (for example, average radius), which can specifically represent such pores, can be smaller than the corresponding radius of the labial following layer. This enables body fluid to move by a capillary phenomenon of the body fluid including menstrual blood without a driving force such as the force of gravity, and it can be further accelerated when there are some driving forces.

Moreover, a capillary phenomenon occurs by wettability of a solid, which is in contact with liquid, and it is possible to accelerate such a phenomenon by surface treatment. The labial following layer set at low density easily deforms in conformity with the shape of a woman's vestibule and the labial inner wall, makes the body fluid, menstrual blood move from the inner wall to the labial following layer between the surface of labial inner wall and the labial following layer, and further can continue to make the body fluid move to the body fluid storage layer by a capillary phenomenon. The structure of the absorbent body can be those where at least a part of the body side of the body fluid storage layer is covered with the labial following layer. The garment side of the body fluid storage layer does not need to be covered with the labial following layer. Therefore, at least a part of the covering material positioned between the labial following layer and the labial inner wall can be water permeable. Also, the covering material, which is in contact with the body fluid storage layer, can have water impermeability.

It is desirable that the "absorbent body" including the labial following layer and the body fluid storage layer shown here is in a state where a third person cannot clearly determine that the absorbent body has at least a two-layer structure, for example, by depositing the labial following layer and the body fluid storage layer so that the density is gradually increased from the body face (upper face) toward the garment face (lower face). Because, in the absorbent body structure substantially regarded as a one layer structure, there is a possibility that degrees of freedom in behavioral changes of the body side (upper face) and the garment side (lower face) of the absorbent body are regulated. Since the absorbent body is at least a two-layer structure including the labial following layer and the body fluid storage layer, the absorbent body can have a structure of three or more layers. It is preferable that the third layer is laid down at a location, which does not inhibit role sharing of labial following property at the body side (upper face) and storage of menstrual blood at the garment side (lower face) of the absorbent body. For example, included is making the third layer intervene between the labial following layer and the body fluid storage layer. The apparent density in the absorbent body is a value of the absorbent body in a location where the ostium vaginae is intended to be in contact by the designer. The measurement method is described below.

(2) The interlabial pad according to (1) wherein said absorbent body side face is in contact with said labial following layer when said body side face of said covering material is in contact with the labia of said wearer.

(3) The interlabial pad according to (1) or (2), wherein said absorbent body has a size, a weight and softness capable of being placed in and retained between labia comfortably, and has a substantially longitudinal shape having longitudinal and lateral directions.

(4) The interlabial pad according to (1) or (2), wherein said absorbent body further comprises a diffusion layer; and said diffusion layer is positioned between said labial following layer and said body fluid storage layer.

"Diffusion layer" can be a layer capable of appropriately dispersing the absorbed body fluid. Also, the diffusion layer can be those which inhibit to give an effect due to the deformation of the labial following layer to the body fluid storage layer. Thin sheet or sheet-like matters can be included in this diffusion layer. It is desirable that the diffusion layer is water permeable and it is possible to use those having various structures and forms such as woven fabrics, knits and paper making. "Being positioned between the labial following layer and the body fluid storage layer" preferably includes a case where a part of the diffusion layer has at least two faces, one face thereof is in contact with the labial following layer whereas another face is in contact with the body fluid storage layer. For example, it is preferable to include a case where one face (tentatively, top side) is in contact with the labial following layer whereas a backside thereof is in contact with the body fluid storage layer when the diffusion layer is a two-dimensionally extending sheet-like matter.

(5) The interlabial pad according to any one of (1) to (4), wherein said diffusion layer has higher Klemm water absorbency than that in the longitudinal direction of said labial following layer.

It is preferable that Klemm water absorbency in the longitudinal direction is higher in the diffusion layer than in the labial following layer. As a specific composition of the diffusion layer, it is preferable that fibers of 100% rayon with a fineness of 1.1 to 4.4 dtx and a fiber length of 25 to 51 mm are entangled by water flow, and mesh-pattering is performed to select spun lace nonwoven fabric with 20 to 50 g/m$^2$ by specific weight per unit and a thickness of 0.2 to 1.0 mm. The diffusion layer can be imparted properties such as that menstrual blood diffusion toward the lateral direction is segmented by performing slit processing directed in the longitudinal direction, that menstrual blood is led in the direct toward the direction of the fibers by making the fiber direct toward the longitudinal direction, and that menstrual blood is led in the longitudinal direction by the capillary phenomenon by performing embossing at a high density area which extends in the longitudinal direction, in order to direct the diffusion area of menstrual blood in the longitudinal direction. However, there is a possibility that a rigid feeling of the diffusion layer is increased if making the fibers direct excessively toward the longitudinal direction or if excessively performing the embossing. More preferable examples include spun lace nonwoven fabric given mesh-patterning by water flow and those given slit processing directed in the longitudinal direction. When making the mesh spun lace nonwoven fabric, capillary force is increased, further Klemm water absorbency in the longitudinal direction is further increased by the slit processing, flexibility as the diffusion layer is enhanced, thereby the labial following layer can be easily deformed. The dimensions of the diffusion layer are not especially limited, however, in order to make the maximum absorbent amount of the body fluid storage layer at a longitudinal area be more easily exploited, it is preferable that the dimension of the diffusion layer in the longitudinal direction is larger than that of the body fluid storage layer.

As a specific composition of the absorbent body, as an example, included is the absorbent body wherein the labial following layer is laminated at a mixture ratio of 60 to 90% of rayon selected from a range with a fineness of 1.1 to 4.4 dtx and a fiber length of 20 to 51 mm and 40 to 10% of natural cotton, the body fluid storage layer is laminated at a mixture ratio of 80 to 99% of pulp selected from a range with a fiber length of 1 to 10 mm and 20 to 1% of particulate absorbent polymer, the resultant fibers are made into a sheet by embossing, and which has a total of 50 to 450 g/m$^2$ by specific weight per unit and a total apparent thickness of 2 to 20 mm. When the whole area of the absorbent body at the garment side of the body fluid storage layer has been covered with the covering material, productivity is enhanced in some cases. The covering material includes tissue set at 15 g/m$^2$ by specific weight per unit as an example.

Therefore, in more suitable examples of the labial following layer, the body fluid storage layer and the diffusion layer, the garment side of the body fluid storage layer is covered with tissue with 10 to 20 g/m$^2$ by specific weight per unit, the pulp selected from a range of fiber length of 1 to 10 mm is laminated at 60 to 120 g/m$^2$ by specific weight per unit in the body fluid storage layer on the upper face thereof, mesh spun lace of rayon with a fineness of 1.1 to 4.4 dtx and fiber length of 25 to 51 mm is laid down in the diffusion layer at the body side of the body fluid storage layer, a mixture at a mixing ratio of 60 to 90% rayon selected from a range of fineness of 1.1 to 4.4 dtx and fiber length of 20 to 51 mm and 40 to 10% of natural cotton is laminated at 150 to 250 g/m$^2$ by specific weight per unit in the labial following layer on the further upper face thereof, and the example can be made into a sheet by dot-shape embossing. The apparent thickness of the labial following layer is preferably from 1.0 to 14 mm, and the apparent thickness of the body fluid storage layer is preferably in a range of 0.6 to 6.0 mm.

(6) The interlabial pad according to any one of (3) to (5), further comprising a folding axis substantially parallel to the longitudinal direction at a substantially center of said lateral direction, and the interlabial pad is retained being placed between the labia of said wearer in a folded state at said folding axis.

The folded state can include the completely folded state and the state where the pad is slightly opened. For example, when folding is performed so that backside sheets are overlapped with one another, the state where the back side sheets are contacted with one another, and the state where they are slightly separated can be included. Also, there can be partially a part folded back.

(7) The interlabial pad according to any one of (1) to (6), wherein said covering material comprises a surface side sheet and a back face side sheet; said surface side sheet is water permeable; said back face side sheet is water permeable or water impermeable; and said covering material covers said absorbent body between said surface side sheet and said back face side sheet.

The covering material can be formed by one type of material, and also including two or more types of materials. Also, the performance such as water permeability can be altered depending on the location of the covering material. This alteration can be performed by changing and attaching materials. Also, even when the materials are the same, the performance can be altered depending on the location by giving a different treatment at a different location.

(8) The interlabial pad according to any one of (3) to (7), wherein said labial following layer and said body fluid storage layer expand in said longitudinal direction and said lateral direction; said labial following layer and said body fluid storage layer are overlapped with one another; and said absorbent body is positioned so that said labial following layer is in contact with said absorbent body side face of said covering material.

(9) The interlabial pad according to any one of (1) to (8), wherein an apparent density of said body fluid storage layer is higher than that of said labial following layer.

It is better that a composition ratio of the apparent thickness which constitutes the absorbent body is set preferably at a range of 60/40 to 95/5 for the labial following layer/body fluid storage layer. The thickness of the interlabial pad in the worn state between the interlabia is preferably from 2 to 20 mm, and more preferably in a range of 4 to 10 mm. Especially when the thickness is less than 2 mm, the thickness becomes smaller (thinner) when absorbing menstrual blood, repulsion force which occurs against the labial interleaving force is weakened, and therefore there is a possibility that the interlabial pad falls from between the interlabia. On the other hand, when it is more than 20 mm, the repulsion force which occurs against the labial interleaving force becomes too large, on the contrary, and not only is the possibility of the interlabial pad falling increased by pushing the right-and-left labia, a foreign feeling is also sometimes given to the wearer. Here, the composition ratio of the apparent thickness which constitutes the absorbent body can be set more preferably at a range of 60/40 to 95/5 for the labial following layer/body fluid storage layer. When the composition ratio of the apparent thickness is set at less than 60/40, the following property in response to behavioral changes of the labial inner wall is reduced or it becomes difficult to reduce a rigid feeling of the body fluid storage layer, and thus there is a possibility that a foreign feeling is given to the wearer. On the other hand, when it is set at more than 95/5, it is considered that it is difficult to transfer menstrual blood acquired at the labial following layer to the body fluid storage layer. The apparent thickness of the absorbent body is preferably in a range of 2 to 20 mm. However, in the interlabial pad worn by being folded (folded in about two) so that the covering materials at the garment side are opposed to one another nearly along the longitudinal direction centerline, the apparent thickness of the absorbent body before being folded is preferably in a range of 1 to 10 mm.

It is preferable that the apparent density of the body fluid storage layer which constitutes the absorbent body is 0.02 g/cm$^3$ or higher than that of the labial following layer, and that the apparent density of the body fluid storage layer is set at 0.07 g/cm$^3$ or more. For example, when the difference in the apparent density of the body fluid storage layer and the labial following layer is less than 0.02 g/cm$^3$, there is a possibility that the flow of menstrual blood by the so-called capillary phenomenon is reduced. The difference of the apparent density of the body fluid storage layer and the labial following layer is preferably in a range of 0.02 to 0.2 g/cm$^3$. The apparent density of the body fluid storage layer is preferably 0.07 g/cm$^3$ or more, and further more preferably in a range of 0.07 to 0.3 g/cm$^3$. For example, when the apparent density of the body fluid storage layer is less than 0.07 g/cm$^3$, since porosity which constitutes the body fluid storage layer is high, it is easily compressed, and thus there is a possibility that menstrual blood once absorbed and stored is released by deformation due to compression. On the other hand, when the apparent density of the body fluid storage layer is more than 0.3 g/cm³, since the porosity which constitutes the body fluid storage layer is too small, it becomes difficult to absorb menstrual blood, and further there is a possibility that a rigid feeling is enhanced.

It is preferable that integrated molding is carried out by an adhesive and embossing in order to prevent interlayer peeling between the labial following layer and the body fluid storage layer. Specific examples of the integrated molding include, for example, embossing. To prevent losing shape in use and to prevent interlayer peeling between the labial following layer and the body fluid storage layer even in a wet state, preferably an emboss rate for the absorbent body area is in a range of 0.6 to 30%. To smoothly transfer menstrual blood absorbed at the labial following layer to the body fluid storage layer, it is preferable that the labial following layer and the body fluid storage layer are integrated without interlayer peeling in use, and thus it is preferable that the embossing is evenly positioned at the absorbent body.

(10) The interlabial pad according to any one of (1) to (9), wherein said labial following layer comprises a first fibrous assembly; said body fluid storage layer comprises a second fibrous assembly; said first fibrous assembly comprises first fibers ; said second fibrous assembly comprises second fibers; and said first fibers are longer than said second fibers.

The labial following layer and/or the body fluid storage layer can be made up of those including a part of the fibrous assembly. For example, the fiber length of the fibers which mainly constitutes the labial following layer can be characterized by being including longer fibers than the fiber length of the fibers which mainly constitutes the body fluid storage layer. When a relatively small amount of menstrual blood is absorbed, sometimes the materials which constitute the absorbent body are drawn to one another by surface tension of menstrual blood, the distance between the materials is shortened, and the apparent thickness of absorbent body is thinned. However, when the fiber length of the fibers which mainly constitute the labial following layer is made longer than the fiber length of the fibers which mainly constitute the body fluid storage layer, even if the labial following layer absorbs menstrual blood, entangled points between the fibers are increased and the distance between the fibers is unlikely to become equal to or less than the fineness. Thus the thickness thereof has difficulty in becoming thin. Therefore, it becomes possible that the labial following layer is easily deformed. One specific composition of the absorbent body is as follows. The labial following layer is made up of one by laminating rayon selected from a range with a fineness of 1.1 to 4.4 dtx and a fiber length of 20 to 51 mm at a mixing ratio of 60 to 90% and natural cotton at 40 to 10%. Also, the body fluid storage layer is comprised of fibers which are made by laminating pulp selected from a range with a fiber length of 1 to 10 mm at a mixing ratio of 80 to 99% and a particulate absorbent polymer at 20 to 1% and is made into a sheet by embossing. These labial following layer and body fluid storage layer can constitute the absorbent body having a total of 50 to 450 g/m² by specific weight per unit and the total apparent thickness of 2 to 20 mm. It is preferable that the relative composition ratio of apparent thickness of the labial following layer to that of the body fluid storage layer is in a range of 60/40 to 95/5. Also, the apparent thickness of the labial following layer is 1.0 to 14 mm, and the apparent thickness of the body fluid storage layer is preferably in a range of 0.6 to 6 mm. Moreover, for "major," when the same substance shows a weight of 60% or more based on the weight of each layer, the substance can be referred to as a major substance.

Compression rigidity (LC) as an index indicating that the labial following layer can be more easily compression-deformed than the body fluid storage layer can be cited. Specific examples shall be given in the following. The labial following layer was made up of rayon with a fineness of 3.3 dtx and a fiber length of 51 mm at a mixing ratio of 85% and natural cotton at 15%, laminated at 180 g/m² by specific weight per unit, and the apparent thickness was set at 2.5 mm. The body fluid storage layer was made up of pulp with a fiber length of 2 to 5 mm at 100%, laminated at 80 g/m² by specific weight per unit, and the apparent thickness was set at 1.0 mm. A test piece (5 cm×5 cm) of each layer was placed on the test table, and compressed by a copper plate with a circular plane of compression area 2 cm² at a velocity of 50 mm/second up to the maximum load of 4900 Pa. The compression rigidity (LC) represents linearity of a compression property (relation of sample distortion and stress given to the sample), and the higher the value is, the higher the rigidity for the compression is. The test piece of the labial following layer shows 0.32 Pa and that of the body fluid storage layer shows 0.41 Pa. This enables to compress and deform the labial following layer more easily than the body fluid storage layer even when the absorbent body becomes a wet state, and thus it is possible to retain the following property to the labial inner wall and to reduce the rigid feeling of the body fluid storage layer with the labial following layer. The wet state shown here indicates the state up to the maximum absorbent amount of each layer.

It is preferable that at the absorbent body of the interlabial pad, a foreign feeling is not given to the wearer by being compressed with less resistance (low resistance) when the body pressure is given whereas when the body pressure is released, the fall off of the interlabial pad is prevented by recovering the thickness. That is, in the absorbent body of the interlabial pad, it is preferable to be compressed with low resistance and show a high recovery rate of thickness, and it is more preferable to have the above functions at the labial following layer opposed to the labial inner wall. In consideration of texture to the skin, performing the slit processing where a rigidity difference is obtained by segmenting fiber entanglement is more preferable than embossing where the rigidity difference is obtained by a density difference. Slit processing can extend in the lateral direction and is disposed in a cross-woven pattern in the longitudinal direction, and includes the slit processing performed by a slit blade with a length of 10 mm. Also, the rigid feeling due to the orientation of the fibers per se can be reduced and flexibility of the absorbent body can be enhanced by making the fiber use no direct orientation when the fibers are laminated. Examples include a process of conveying so that the tensile force to the absorbent body after laminating the fibers. An index of the fiber direct orientation includes a ratio of the maximum tensile strength in the longitudinal direction, i.e., a value obtained by dividing the tensile strength in the longitudinal direction by the maximum tensile strength in the lateral direction, of the absorbent body where embossing is performed to the fiber assembly where the fibers are laminated by rollers each having flat faces, and it is preferable that it is 40 or less.

(11) The interlabial pad according to (6), wherein said covering materiel comprises a surface side sheet and a back face side sheet; said surface side sheet is water permeable; said back face side sheet is water permeable or water impermeable; said covering material comprises said absorbent body between said surface side sheet and said back face side sheet; the interlabial pad further comprises a long convex area which forms a top part toward the body side of the wearer in a state where said surface side sheet extrudes from the surface by being folded along said folding axis so that the back face side sheets are opposed to each other; an extending area which is extends from both sides of said long convex area in the lateral direction; and said body fluid storage layer is positioned at the side of the back face side sheet closer than said labial following layer, and a part of said body fluid storage layer is positioned at said long convex area.

Since both side parts of the body fluid storage layer where menstrual blood is stored become difficult to be in contact with combined pads or garments by not installing the body fluid storage layer at both side parts of the extending area, it is possible to prevent leakage of menstrual blood onto the combined pads or the garments from the left-and-right direction of the interlabial pad. Furthermore, the adhesive areas of the labial following layer not only to the labial inner wall but also to the pudendum are increased by making the labial following layer extended to the extended area, therefore, it is possible to prevent leakage of menstrual blood. At least a part of the body fluid storage layer can be positioned at the long convex area. It is preferable that it is not positioned at an area (top part) nearly along the centerline extending in the longitudinal direction. Because it is considered that a rigid feeling of the body fluid storage layer is given to the wearer by a motion such as sitting on a chair, a foreign feeling is easily given when the body fluid storage layer is positioned at the location opposed to the vestibule since the density of the body fluid storage layer is set to become high.

(12) The interlabial pad according to (7) or (11), wherein a miniature sheet piece is attached to said back face side sheet. When the long convex area is formed and a space whole sectional shape is triangular remains underneath thereof, a miniature sheet piece can be attached at the site corresponding to a bottom line of the triangle. It is preferable that an opening of the triangle made in this manner is made so that a finger of the wearer can be inserted. While wearing it between the interlabia, the labia can be pushed and opened by stiffness of the finger by contacting the finger in the vicinity of the longitudinal direction centerline at the garment side of the interlabial pad, therefore, the interlabial pad can be reliably worn in the vestibule and it becomes possible to eliminate space between the body side of the interlabial pad and the vestibule or the interlabial inner wall. In order to contact the finger in the vicinity of the longitudinal direction centerline at the garment side of the back face side sheet, a finger insertion opening capable of securing the finger in the longitudinal direction of the back face side sheet can be formed, by providing a miniature sheet piece which one or more joint parts at the both sides of the longitudinal direction of the garment side of the back face side sheet, and one or more non-joint parts at the lateral direction of the back face side sheet are joined. In the interlabial pad comprising the miniature sheet piece having the finger insertion opening at the garment side, the ostium vaginae position which is a concave part can be detected by a fingertip excellent in sensitivity by inserting the finger so that a fingerprint surface is contacted with the back face side sheet, thereby the interlabial pad can be worn at an accurate position. The shape of interlabial absorbent layers is not especially limited as long as it is a shape capable of being placed between a woman's interlabia, and is not especially limited as long as it is a form, which fits a woman's interlabial area.

Figure 1:
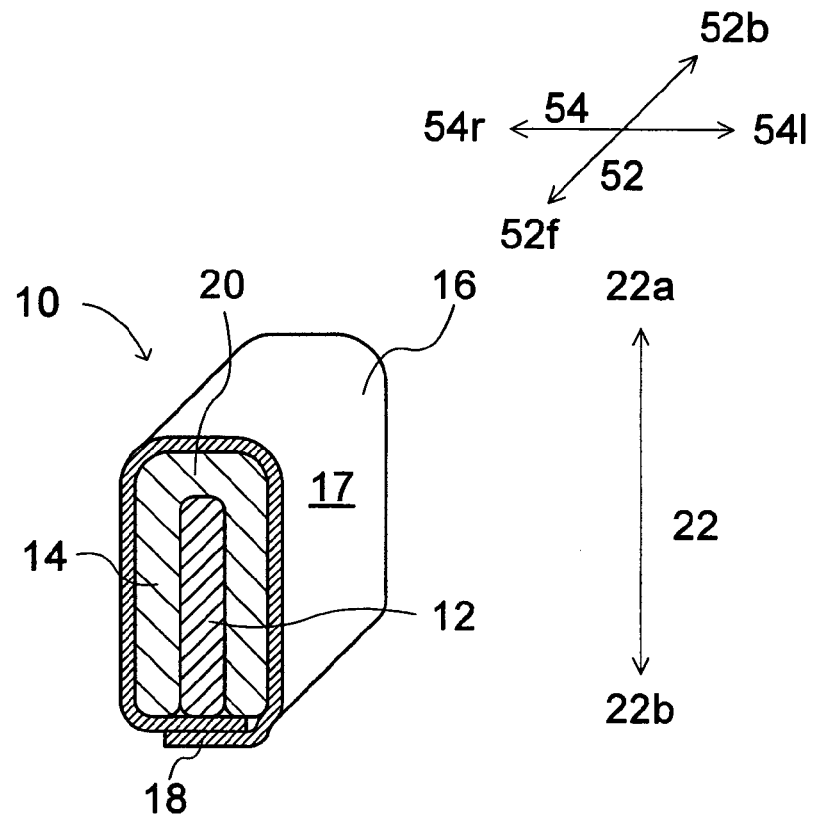
FIG. 1 is a perspective view including a cross sectional of an interlabial pad which is the first embodiment of the present invention.

DESCRIPTION OF THE PREFERRED EMBODIMENT.

Next, one embodiment of the interlabial pad of the present invention is described with reference to the figures, however, the present invention is not limited thereto. Moreover, the same signs denote the same members or the same parts unless otherwise specified.

[Whole Shape]

In one aspect of the interlabial pad of the present invention, the interlabial pad with a shape capable of being placed between a woman's interlabia comfortably, comprising an absorbent body which absorbs body fluid and a covering material which covers the absorbent body, wherein the absorbent body is including a labial following layer which is located at the body side and the body fluid storage layer which is located downward thereof (garment side) and of which the body side is covered with the labial following layer, and is characterized in that the labial following layer is compressed more easily than the body fluid storage layer and thus deformation is easy when the interlabial pad is worn, and in that the apparent density of the labial following layer is lower than that of the body fluid storage layer. In this absorbent body, the labial following layer which is capable of being compressed and deformed more easily than the body fluid storage layer is positioned in the vicinity of the labial inner wall, therefore, even when the labia are inflected in the right-and-left direction along an axis of the vertical direction, and the convex and concave shape of the labial inner wall is deformed, the labial following layer can be easily compressed and deformed in response to behavioral changes of the labial inner wall. Furthermore, it is considered that a foreign feeling is not easily given to the wearer because the body side of the body fluid storage layer is covered with the labial following layer and thus rigid feeling of the body fluid storage layer can be simultaneously reduced by the labial following layer.

It is preferable that it is the same in a dry state as well as in a wet state where menstrual blood is absorbed that the labial following layer is compressed and deformed more easily than the body fluid storage layer. It is preferable that the labial following layer is easier in deformation and the like than the body fluid storage layer. For example, it is preferable that the compression rigidity (LC) is a lower value in the labial following layer than in the body fluid storage layer regardless of the states of drying and wetting. It is considered that even when the absorbent body becomes a wet state while wearing, the labial following layer easily follows the morphological changes of the labial inner wall prior to the body fluid storage layer, and thus the absorbent body has flexibility, which can reduce the rigid feeling of the body fluid storage layer. It is possible to prevent from directly carrying the rigid feeling of the body fluid storage layer of which apparent density is high to the labial inner wall by positioning the labial following layer at the body side (can be the face directed to the covering material which is in contact with the body, especially the labia) of this body fluid storage layer. Furthermore, even when the interlabial depth change occurs by an individual difference or behavioral changes, no space due to the thickness of the body fluid storage layer is allowed to occur to the lateral dimension of the labial following layer larger than that of the body fluid storage layer in the absorbent body, therefore, the labial following layer can retain adhesiveness to the labial inner wall and further to the pudendum, and it becomes possible to prevent menstrual blood leakage.

Also, the labial following layer where the density is set to be low is placed in the vicinity of the labial inner wall and the body fluid storage layer where the density is increased is placed at a lower face thereof (garment side), therefore, it is possible to acquire menstrual blood at the labial following layer for the discharge pathway with a high rate and at a large amount which flows downward along the labial inner wall and continues to transfer to the body fluid storage layer by a capillary phenomenon between the labial following layer and the body fluid storage layer, and thus it is possible to acquire at the labial following layer even when menstrual bloods discharged again. By this, there is a possibility that, in the absorbent body including the labial following layer and the body fluid layer, a saturated state of absorption tentatively occurs at the labial following layer due to the absorption of menstrual blood, however, the absorbed menstrual blood is transferred to the body fluid storage layer, therefore, the maximum absorbent amount of the absorbent body is exploited, and thus it is possible to prevent leakage even if menstrual blood is in a large amount.

Also, menstrual blood is accumulated from the body fluid storage layer which is the garment side of the absorbent body, therefore, it is not easily retain menstrual blood on the surface of the interlabial pad which is in contact with the body such as the labia and fluidity caused by the retained menstrual blood is inhibited, and thus it is possible to retain the contact area of the labial inner wall with the interlabial pad surface. Therefore, it becomes possible to prevent fall off of the interlabial pad. Here, when the body fluid storage layer is easily compressed similarly to or compressed and deformed more easily than the labial following layer, if a space between the fibers due to whole deformation is easily deformed, menstrual blood once stored at the space is easily released again. Therefore, not only the is possibility increased that menstrual blood is leaked through the labial following layer again or through another pathway, also the possibility is increased that menstrual blood which has returned to the surface of the interlabial pad is retained and the interlabial pad falls. The evaluation method of the maximum absorbent amount as the absorbent body shown here is described below.

As the structure of the absorbent body, the body side of the body fluid storage layer can be covered with the labial following layer. That is, a foreign feeling should not be given to the wearer by making the labial following layer capable of being easily compressed and deformed opposed to the labial inner wall and easily deforming it. Thus the garment side of the body fluid storage layer does not need to be covered with the labial following layer.

[Interlabial Pad of the First Embodiment]

FIG. 1 shows a sectional view of the interlabial pad 10 of the present embodiment. In FIG. 1, the absorbent body at the body side of the body fluid storage layer 12 covered with the labial following layer 14 is covered with the covering material 16 which is a liquid permeable material. To show a positioning direction of the interlabial pad 10, an upper side in the figure is made the body side 22a and a lower side in the figure is made the garment side 22b. The covering material 16 covers the absorbent body by forming a covering material overlapping part 18 at a bottom in the figure. Also, the overlapping part 18 can be a tab to remove the worn interlabial pad 10.

Crossing lines 52 and 54 at the upper side in the figure show a two-dimensional position relationship of the interlabial pad 10. That is, a near side and a far side in the figure correspond to a front 52f and a back 52b of the interlabial pad 10, respectively. A right side and a left side toward the FIG. 10 correspond to a right hand 54r and a left hand 54l of the interlabial pad 10, respectively. In this interlabial pad 10, a cross direction is longitudinal, this direction is the longitudinal direction and a right-and-left direction is the lateral direction.

Said labial following layer 14 can be easily compressed and deformed, follows morphological changes of the labial inner wall to adhere, and simultaneously reduces the rigid feeling of the body fluid storage layer 12. Also, the body fluid is acquired at the labial following layer 14, it is possible to continue to transfer the body fluid by a capillary phenomenon with the body fluid storage layer 12, and thus, it is possible to prevent body fluid leakage from the labial following layer 14 close to the labia.

Also, when wearing the interlabial pad 10, the covering materials 16 at the garment side are worn by being folded facing one another along the longitudinal direction centerline, the right-and-left body sides 17 of the interlabial pad with a symmetric axis of the longitudinal direction centerline opposed to right-and-left labia easily follow the behavioral changes of right-and-left labia involved in motion changes of the wearer, and therefore, it becomes possible that a space does not easily occur between the body sides of the interlabial pad 10 and the vestibule or the labial inner wall. Moreover, an absorbent body of which the body side and the garment side of the body fluid storage layer 12 are covered with the labial following layer 14 can be used. This makes the labial following layer 14 at the body side and the labial following layer 14 at the garment side share their roles. That is, it is considered that the body side of the labial following layer 14 at the body side follows the behavioral changes of the labial inner wall and is easily compressed and deformed, the labial following layer 14 at the garment side has the role of a so-called cushion layer which reduces the rigid feeling of the body fluid storage layer 12, therefore, not only is a foreign feeling further difficult to be given to the wearer, it is also possible that outside pressure is difficult to be given to the body fluid storage layer 12 where menstrual blood is stored, and thus it is possible to prevent flowback of menstrual blood from the body fluid storage layer 12.

It is desirable that a third person cannot determine that the absorbent body is clearly made up of at least a two-layer structure including the labial following layer 14 and the body fluid storage layer 12, for example, by depositing so that the density is gradually increased from the body side 22*a* toward the garment side 22*b*. Since the structure of said absorbent body is substantially regarded as a single layer structure, degrees of freedom of which are regulated for respective behavioral changes at the body side 22*a* and the garment side 22*b* of the absorbent body, it is thus considered difficult to make role sharing of the following property to the labia at the body side 22*a* and storage of menstrual blood at the garment side 22*b* in the absorbent body compatible. The meaning "at least two structures" is that the absorbent body can be of a three or more layer structure, however, it is desirable that a third layer is laid down at a position which does not inhibit the role sharing of the following property to the labia at the body side 22*a* and storage of menstrual blood at the garment side 22*b* of the absorbent body, and an example where the third layer is made to intervene between the labial following layer 14 and the body fluid storage layer 12 can be cited. The apparent density in the absorbent body is a value of the absorbent body at a position where the ostium vaginae is intended to be in contact by the designer, and is converted from the volume and weight of the absorbent body measured under the following conditions. The position where the ostium vaginae is intended to be in contact by the designer is carefully described because most designers design intending an absorbent body to be in contact with the ostium vaginae on a longitudinal axis centerline in the lateral direction, and do not necessarily design intending the absorbent body to be in contact with the ostium vaginae on a lateral axis centerline in the longitudinal direction.

[Method for Measuring the Apparent Density]

The method for measuring the apparent density described above is explained in due order. (1) First, the absorbent body at a position in contact with the ostium vaginae in the longitudinal direction was cut in the lateral direction, and a cross sectional area of the absorbent body at 5 mm each right and left (total 10 mm width) from the longitudinal axis centerline was measured. A measuring direction of the cross sectional area of the absorbent body is not limited as long as the measurement can be performed with no load, and in this case, the cross sectional area was measured by a digital microscope (Keyence Corporation, VH-6200). When the absorbent body is not a plane shape such as being folded and being totally wave-like formed by embossing, the area was measured by outspreading it to a plane shape so as not to affect the cross sectional area. Even when the absorbent body is made up of two layers, the cross sectional area of each layer was measured at such a state. (2) Next, in another absorbent body sample, as a position in contact with the ostium vaginae as a center, the sample was cut at a position of 5 mm to respective right and left directions (total 10 mm width) and a position of 5 mm to respective cross directions (total 10 mm width). (3) And, the weight of the sample obtained at step (2) cut into a size of 10 mm×10 mm was measured. At this time, even when respective layers are integrated by an adhesive or embossing, they were separated so that a weight change in each layer would not occur wherever possible. (4) Further, a volume was obtained by multiplying the cross sectional area (a step of (1)) measured under no load by the area of 10 mm×10 mm. (5) At a weight (step (3) measured under the above-mentioned conditions was divided by the volume (step (4)) of N=10, the resultant value was made to be an apparent density in the present invention.

Also, even when the material which constitutes each layer was made up of multiple types, for example, even when the absorbent body is constituted by mixing fibrous rayon and a particulate absorbent polymer, it is possible to obtain the apparent density at each layer by the above measuring method. Moreover, in a sample where the size is not 5 mm in the respective right and left directions from the longitudinal direction axis centerline in the above step (1), the cross sectional area in a feasible range from the longitudinal axis centerline is measured, the sample cutting shown in the above step (2) is performed in conformity with the range, and the weight is measured. Because, the apparent density does not vary depending on the size of sample cutting, the size of the sample cutting can be appropriately changed in conformity with the size of the sample.

Again returning to FIG. 1, this is described in greater detail. As mentioned above, the interlabial pad 10 which is the first example of the present invention is made up of the body fluid storage layer 12 positioned at an innermost part, the labial following layer 14 surrounding a periphery thereof, and the covering material 16 which encloses and covers them. The interlabial pad 10 exhibits a columnar shape with slight roundness and a sectional long rectangle in this figure, and at both ends thereof, the cross sectional areas become smaller, it is possible to make it into a quadrangular pyramid shape. In the covering material 16 of the interlabial pad 10, the covering material overlapping part 18 is formed at the garment side 22*b*, and by closing here, it is possible to cover the above body fluid storage layer 12 and labial following layer 14. The above-mentioned covering material overlapping part 18 can be used as a tab to remove the interlabial pad 10. Both side faces of the covering material 16 have body sides which are in contact with the labial inner wall (not shown in the Fig.) being sandwiched by the labia, and a top part of the interlabial pad 10 is made to contact with the body. The above surface of the covering material 16 is mainly called the body side of the covering material. Moreover, the back side face of the body side of the covering material 16 can be called an absorbent body side because it is in contact with the absorbent body (one comprising the body fluid storage layer 12 and the labial following layer 14).

The body fluid storage layer 12 extends longitudinally and vertically in the section thereof, and the both sides and the top part thereof are in contact with the labial following layer 14. Here, "in contact with" can mean to directly or indirectly come close to one another, and can generally mean a state where a mechanical or dynamic effect is given. Especially when the flow of menstrual blood becomes a matter of discussion, it can mean a state where this flow is affected. The labial following layer 14 can flexibly follow morphological changes of the labial inner wall and change into the shape thereof. Menstrual blood can pass through the covering material 16 of the interlabial pad 10, and reach the body fluid storage layer 12 through the labial following FIG. 1. It can flexibly follow the morphological changes of the labial inner wall and change the shape thereof, therefore, it is unlikely to bring about a space between the labial inner wall, and thus, it is possible to effectively prevent leakage of menstrual blood attributed to the space.

Figure 15:
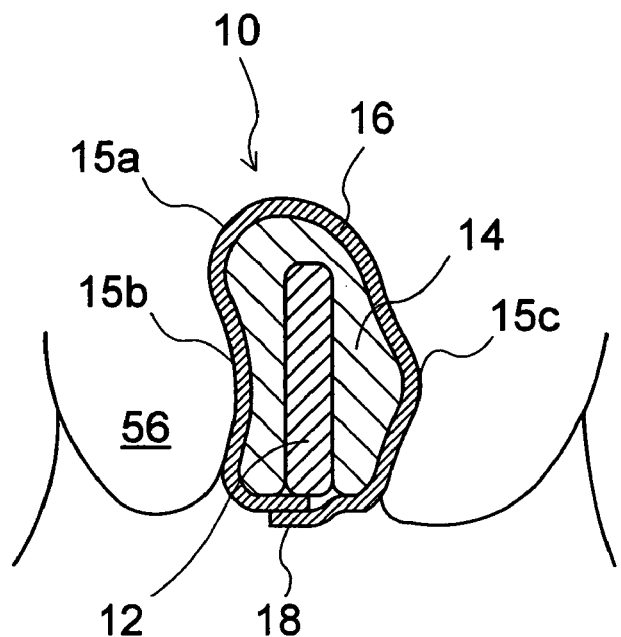
FIG. 15 is a sectional view showing a wearing state of the interlabial pad which is the first embodiment of the present invention.
Figure 16:
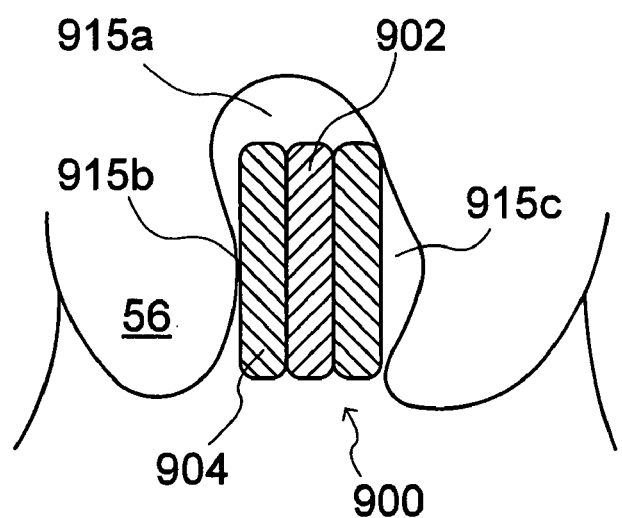
FIG. 16 is a sectional view showing a state while wearing a comparative example.

This is described in greater detail with reference to FIGS. 15 and 16. FIG. 15 shows a state where the interlabial pad 10 in FIG. 1 is worn being placed between labia 56. In the labial inner wall, the convex -concave shape thereof is deformed due to the posture of the wearer. For example, the labial following layer 14 moderately curves like the part 15a and the part 15b in accordance with the shape of labial inner wall. Also, the labial following layer 14 protrudes to the right side toward the figure like the part 15c. In the interlabial pad 10, which is the first example of the present invention, the labial following layer 14 and the covering material 16 flexibly respond to these deformations to adhere to the labial inner wall. Thus, it is possible to effectively prevent leakage of menstrual blood, which is easily brought about from the space. On the contrary, as a comparative example, FIG. 16 shows a wearing state of an interlabial pad 900 where members 904 with high density and high stiffness are positioned at both sides and the member 902 with low density and low stiffness is positioned at the center. As in FIG. 15, the labia is deformed, however, the member 904 with high density and high stiffness does not follow this deformation well, and thus a space 915a is made at the upper side (body side) of the interlabial pad 900. A space 915b is also made at the left side toward the figure of the interlabial pad 900. Additionally, at the right side toward the figure of the interlabial pad 900, there is a part where the member 904 with high density and high stiffness is in contact with the labial inner wall at a small area, the member 904 is not deformed, and thus there is a reason for making a space 915c at a periphery thereof.

[Interlabial Pad of the Second Embodiment]

Figure 2:
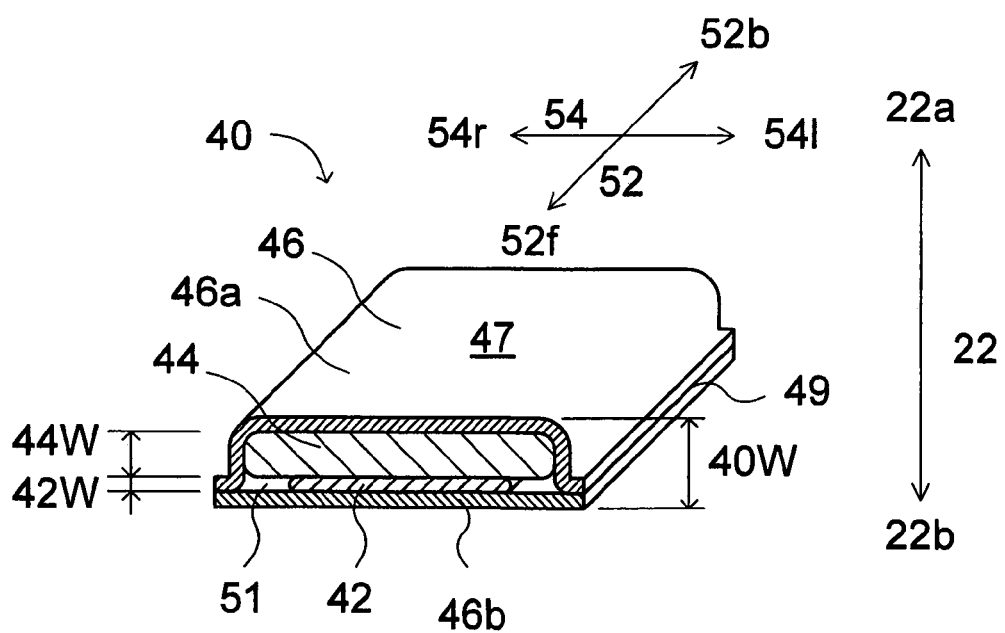
FIG. 2 is a perspective view including a cross sectional of an interlabial pad which is the second embodiment of the present invention.

FIG. 2 shows the second example of the present invention. A vertical line in the figure shows the position relationship of the body side and the garment side of the interlabial pad 40 as in the case of the above, and crossing lines 52 and 54 at the middle upper side in the FIG. 2 show the plane position relationship of the interlabial pad 40. That is, a near side and a far side in the figure correspond to a front 52f and a back 52b of the interlabial pad 40, respectively. A left side and a right side toward the figure correspond to a right hand 54r and a left hand 54l of the interlabial pad 40, respectively. In this interlabial pad 40, a cross direction is longitudinal, this direction can also be called the longitudinal direction and the right-and-left direction can be called the lateral direction. In this interlabial pad 40, the body fluid storage layer 42 two-dimensionally extends nearly along the plane made up of the above crossing lines 52 and 54, and thereon the body fluid storage layer 42 similarly. two-dimensionally extends at a face of the garment side in contact with a face of the body fluid storage layer 42. However, the labial following layer 44 is wider than the body fluid storage layer 42, and thus spaces 51 are formed at both sides of the body fluid storage layer 42. This way, the absorbent body made up of the body fluid storage layer 42 and the labial following layer 44 is positioned on the back face side sheet 46b (extends similarly two-dimensionally) which is a component of the garment side 22b of the covering material 46. Right and left side end parts 49 of this back face side sheet 46b are joined at the side end parts of the surface side sheet 46a which is a component of body side 22a of the covering material 46, and the surface side sheet 46a covers the absorbent body (including the body fluid storage layer 42 and the labial following layer 44). The surface side sheet 46a is in contact with the labial inner wall at the body side 47 thereof. The back face side sheet 46b has the garment side at the lower side thereof (garment side 22b). As in the above, in the second example in FIG. 2, the body fluid storage layer 42 is in contact with the labial following layer 44 only at the face which is present at the body side.

Figure 3:
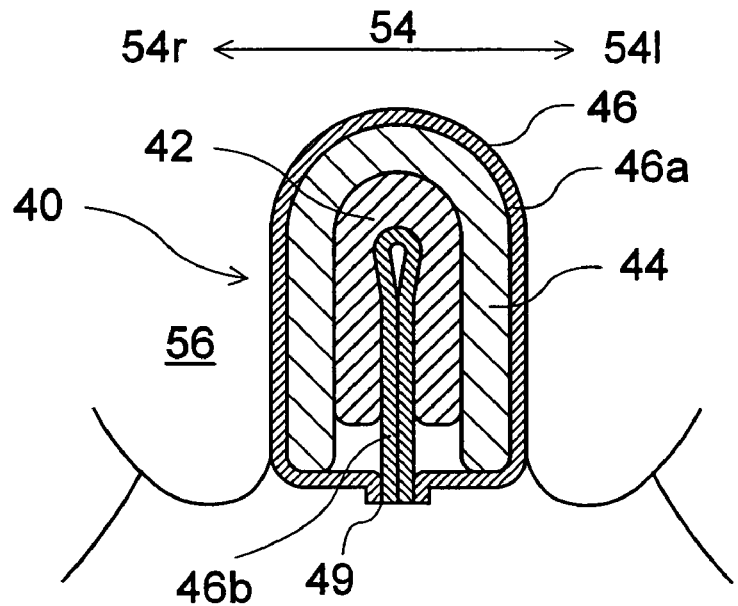
FIG. 3 is a view showing a wearing state of an interlabial pad which is the second embodiment of the present invention.

FIG. 3 shows the wearing state where the interlabial pad 40 of the second example in FIG. 2 is worn being placed between the interlabia. The interlabial pad 40 in FIG. 2 is placed between the right-and-left labia 56 being folded in two along a folding axis nearly along the cross direction so that the back face side sheets 46b of the covering material 46 are overlapped with one another. Therefore, the body side of the surface side sheet 46a of the covering material 46 comes into contact with the labial inner wall and labial back wall. The interlabial pad 40 is worn between the interlabia by such wearing in substantially the same shape as that in FIG. 1. Therefore, most of the menstrual blood is absorbed in the body fluid storage layer 42 through the body side face, and thus the back face side sheet 46b can be water impermeable. Moreover, the space 51 in FIG. 2 becomes slightly small by being folded, however, it is left as a space in the folded state.

[Interlabial Pad of the Third Embodiment]

Figure 4:
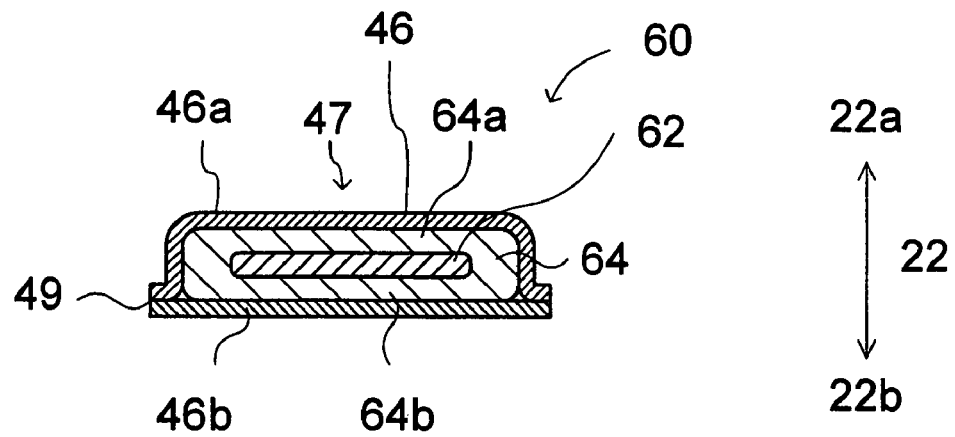
FIG. 4 is a sectional view of an interlabial pad which is the third embodiment of the present invention.

FIG. 4 is a sectional view showing the interlabial pad 60 which is the third example of the present invention. The surface side sheet 46a and the back face side sheet 46b of the covering material 46 enclose and cover the absorbent body made up of the body fluid storage layer 62 which extends right-and-left nearly at a center part and the labial following layer 64 which surrounds said body fluid storage layer 62. The surface side sheet 46a and the covering material 46 are joined at the side ends 49 thereof. Therefore, this interlabial pad 60 can be worn between the interlabia as it is, or can be worn being folded in two as in FIG. 3. In the former case, said interlabial pad 60 is raised, and the left-and-right parts of the labial following layer 64 are positioned at the body side 22a and the garment side 22b, respectively. At this time, the upper part 64a and lower part 64b of the labial following layer 64 are deformed by following the shape of the right and left labial inner wall. In the latter case, the interlabial pad 60 is folded so that the body side face 47 is outside, and the face is in contact with the labial inner wall to change the form thereof.

[Interlabial Pad of the Fourth Embodiment]

Figure 5:
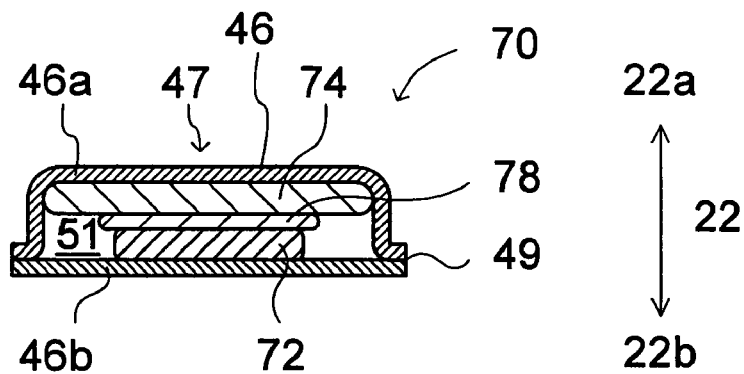
FIG. 5 is a sectional view of an interlabial pad which is the fourth embodiment of the present invention.

FIG. 5 is a sectional view showing the interlabial pad 70 which is the fourth example of the present invention. The similarly extending diffusion layer 78 is positioned on the body fluid storage layer 72 which extends right-and-left nearly at the center part. Additionally, thereon, the labial following layer 74 which similarly extends is positioned. As in the case of the example in FIG. 2, since the width of the body fluid storage layer is narrow, the space 51 remains. The absorbent body made up of the body fluid storage layer 72, the diffusion layer 78 and the labial following layer 74 is covered with the surface side sheet 46a and the back face side sheet 46b of the covering material 46 which are joined at respective side end parts 49. This interlabial pad 70 can be worn between the interlabia being folded in two as in FIG. 3. At this time, the interlabial pad 70 is folded so that the body side face 47 is outside, and the face is in contact with the labial inner wall to change the form thereof. The menstrual blood, which comes from the body side 47, is once absorbed in the labial following layer 74, appropriately diffused at the diffusion layer 78, and absorbed in the body fluid storage layer 72 beneath it at a wide area. It is considered that this makes the absorption at the body fluid storage layer 72 uniform and absorption ability such as the absorption rate improves.

[Interlabial Pad of the Fifth Embodiment]

Figure 6:
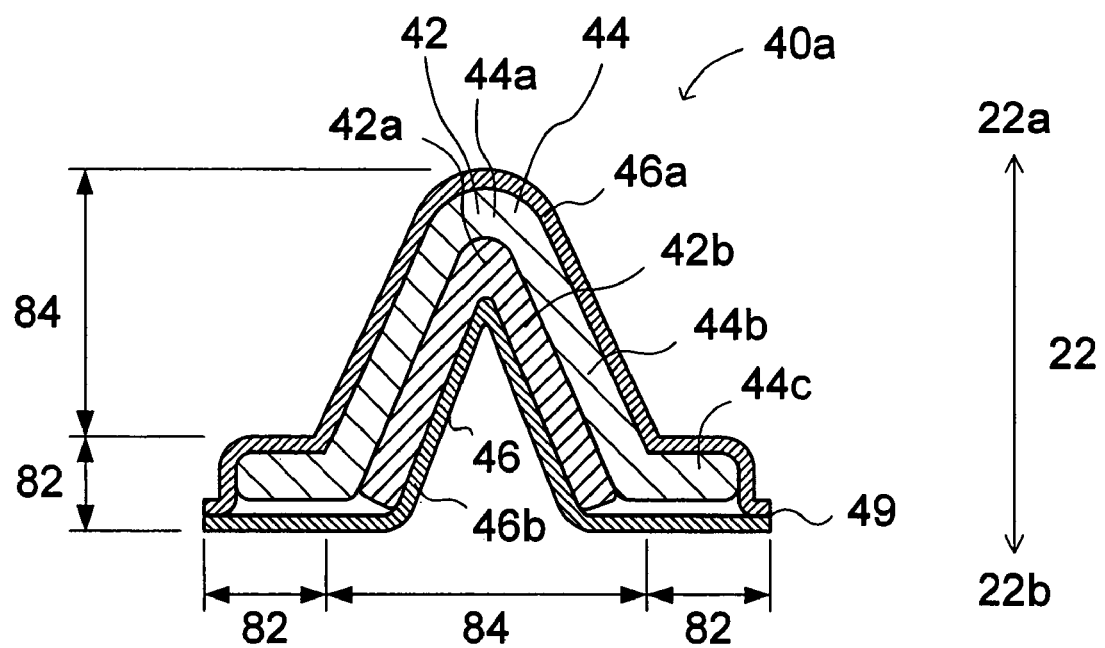
FIG. 6 is a sectional view of an interlabial pad which is the fifth embodiment of the present invention.

FIG. 6 shows the interlabial pad 40a which is an additional fifth example of the present invention which is made into a desired shape by further performing processing such as folding. This interlabial pad 40a exhibits a shape such as a brimmed hat with an aculeate triangle top in the sectional shape, and has the following characteristics in the right-and-left direction or the height direction. There is a long convex area 84 in the right-and-left center part (or in the height direction body side), which is the part being placed between the interlabia. Also, there is an extending area 82 formed extending from both side parts of this long convex area toward the lateral direction, which is typically not placed between the interlabia however, it is an area in contact with the body. On the other hand, respective members which are the same components as those in FIG. 2, the body fluid storage layer 42 is positioned on the surface at the body side 22a of the back face side sheet 46b, and the labial following layer 44 is positioned thereon. Additionally, thereon, the surface side sheet 46a is positioned, and the entire absorbent body is covered with the covering material 46 made up of the surface side sheet 46a and the back face side sheet 46b joined at the side end parts 49 thereof. At this time, the space 51 observed in FIG. 2 corresponds to a bottom of a bottom part 44c of the labial following layer 44, and said space 51 nearly disappears being folded back in a brim shape. The absorbed menstrual blood is absorbed through the surface side sheet 46a, and thus menstrual blood which has passed through the long convex area 84 of the surface side sheet 46a placed between the interlabia is absorbed to a top part 44a and side parts 44b of the labial following layer 44 in contact with the garment side of the surface side sheet 46a. The bottom part 44c of the labial following layer 44 which is located at the extending area 82 absorbs menstrual blood which comes out of the labia along the labial inner wall and menstrual blood which moves from the side part 44, however, the amount thereof is inferred as being significant. The menstrual blood once absorbed in the top part 44a and the side parts 44b of the labial following layer 44 is further transferred to the body fluid storage layer 42 by a capillary phenomenon. There is no body fluid storage layer 42 at the garment side of the bottom part 44c of the labial following layer 44, however, since it is inferred that a significant amount of the menstrual blood is not absorbed in the bottom part 44c as described above, it does not interfere with the function of the interlabial pad. Positioning the body fluid storage layer 42 in this manner makes it easier to fold back the interlabial pad for forming the extending area 82 because a fold line does not become thick.

[Interlabial Pad of the Sixth Embodiment]

Figure 7:
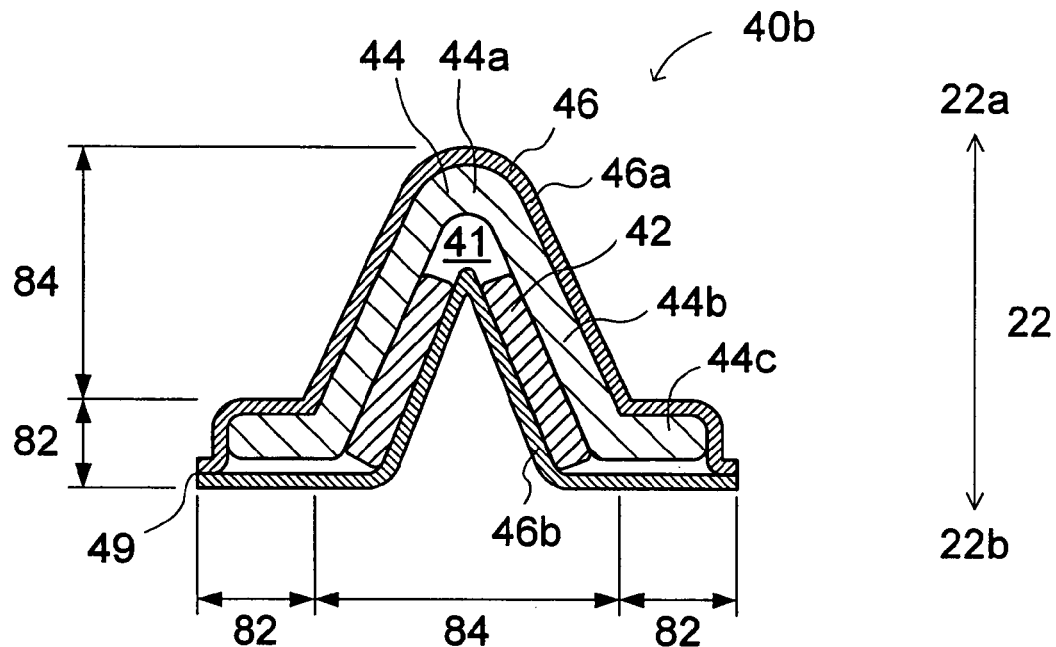
FIG. 7 is a sectional view of an interlabial pad which is the sixth embodiment of the present invention.

FIG. 7 shows the interlabial pad 40b which is the sixth example of the present invention different from the fifth example in FIG. 6 in terms of the body fluid storage layer 42 being divided into two. In this example, the composition is the same except that the space 41 is formed at a position shown by 42a in FIG. 6, and thus redundant description with the above is omitted. In this example, the body fluid storage layer 42 is positioned being divided into two at the surface of the garment side 22b of the labial following layer 44, more particularly, it is not positioned at the garment side 22b of the top part 44a of the labial following layer 44, and the divided body fluid storage layers 42b are positioned on the garment sides 22b of both side parts 44b. Moreover, it is the same as the fifth example in that it is not positioned at the garment side 22b of the bottom part 44c of the labial following layer 44. When the space 41 is made at the part at which the top part is located in this manner, it becomes easier to fold the interlabial pad 40b along a folding axis in the vicinity of the top part of the interlabial pad 40b.

[Interlabial Pad of the Seventh Embodiment]

Figure 8:
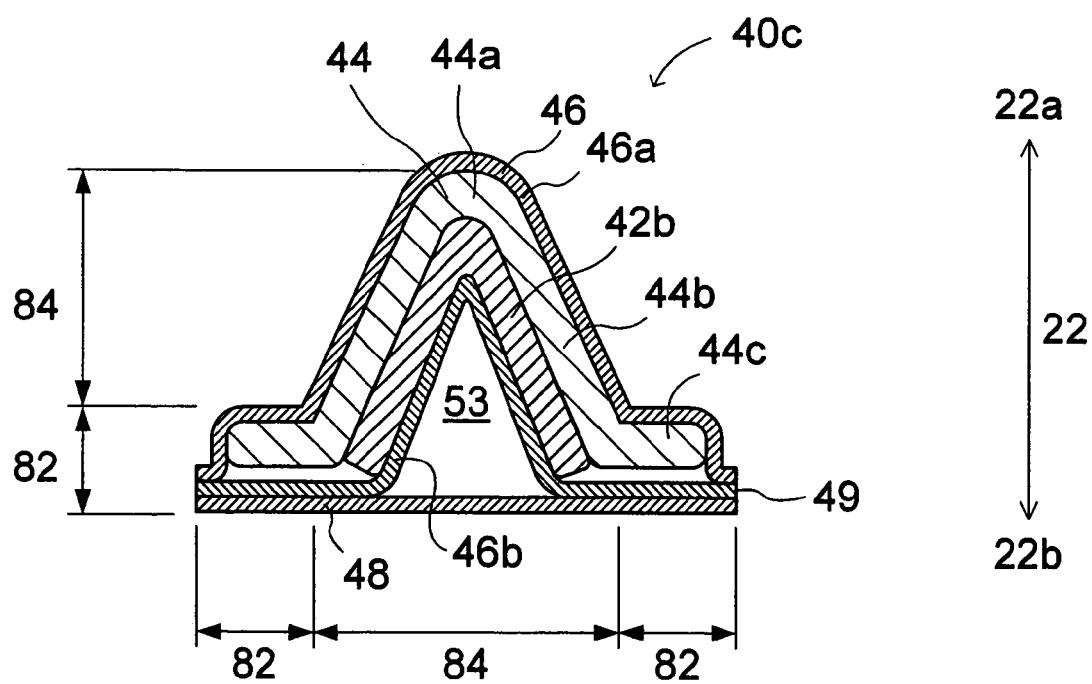
FIG. 8 is a sectional view of an interlabial pad which is the seventh embodiment of the present invention.

FIG. 8 shows the interlabial pad 40c which is a seventh example where a miniature sheet piece 48 is attached to the fifth example in FIG. 6. It is the same as the fifth example except for that the miniature sheet piece 48 is attached, and thus redundant description is omitted. The miniature sheet piece 48 is joined at the right-and-left side end parts 49 thereof together with the side end parts 49 of the back face side sheet 46b and/or the surface side sheet 46a of the covering material 46. At this time, it can be or cannot be joined to the back face side sheet 46b at the extending area 82. The triangular space 53 made beneath the long convex area 84 can be rendered a finger insertion hole for wearing the interlabial pad 40c. When such a miniature sheet piece 48 is attached, it becomes easy to stabilize the shape of long convex area 84.

FIGS. 9 to 14 show states where various interlabial pads 40 having the long convex area 84 with various dimensions of the body fluid storage layers 42 and labial following layers 44 are worn. In these figures, other members such as the covering material are not shown for easier understanding.

Figure 9:
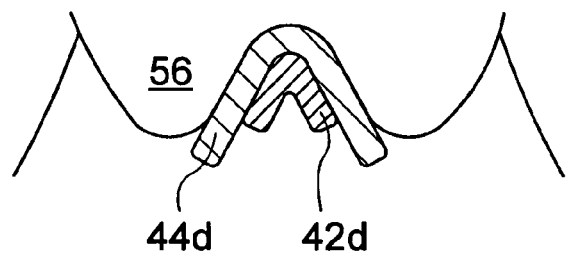
FIG. 9 is a sectional view showing a wearing state of the interlabial pad of the present invention.

In FIG. 9, shown is a state where the wearer possessing the labia with an average depth wears an interlabial pad of which the length in the lateral direction of the labial following layer 44d is longer than that of the body fluid storage layer 42d. Since the labial following layer 44d is longer than the total length of labia 56 inner wall in the lateral direction, the end part thereof in the lateral direction protrudes.

Figure 10:
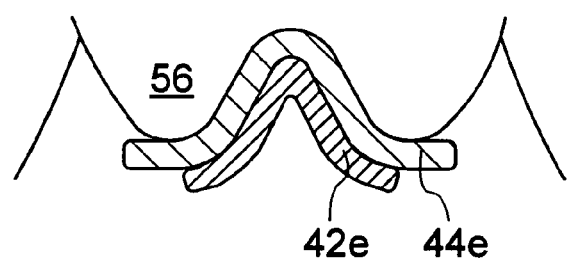
FIG. 10 is a sectional view showing a wearing state of the interlabial pad of the present invention.

FIG. 10 shows a state where a wearer with a shallow labia wears an interlabial pad of which the lateral direction length of the body fluid storage layer 42e is slightly shorter than that of the labial following layer 44e as in FIG. 6.

Figure 11:
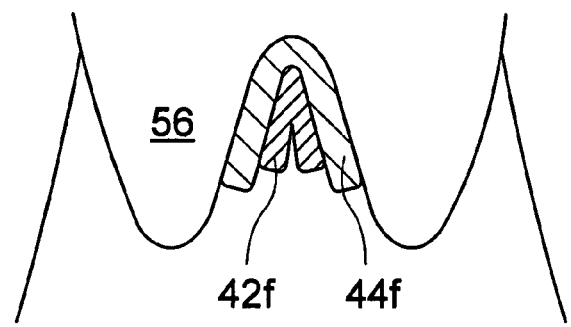
FIG. 11 is a sectional view showing a wearing state of the interlabial pad of the present invention.

FIG. 11 shows a state where a wearer with slightly deep labia wears the interlabial pad of which the length in the lateral direction of the labial following layer 44f is longer than that of the body fluid storage layer 42f. Since the length in the lateral direction of the labial following layer 44f is shorter than the total length of the labia 56 inner wall, all of the labial inner wall is not in contact with the labial following layer 44f.

Figure 12:
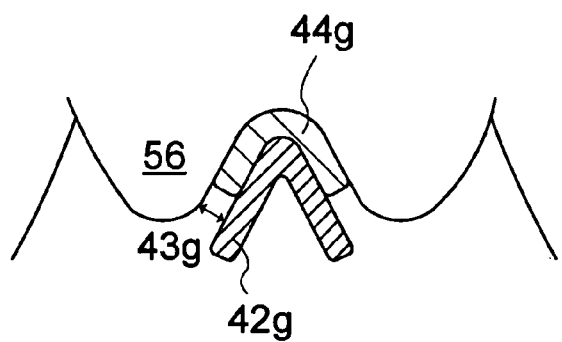
FIG. 12 is a sectional view showing a wearing state of the interlabial pad of the present invention.
Figure 13:
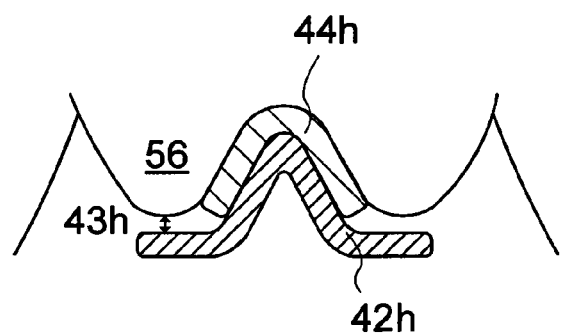
FIG. 13 is a sectional view showing a wearing state of the interlabial pad of the present invention.
Figure 14:
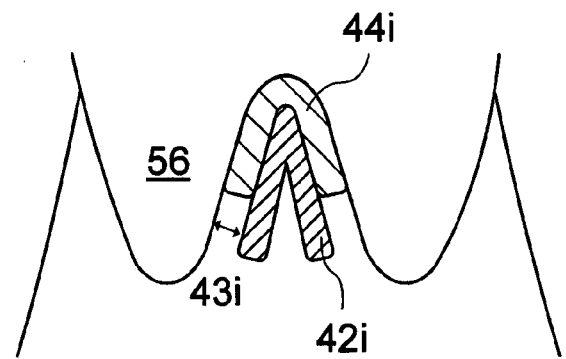
FIG. 14 is a sectional view showing a wearing state of the interlabial pad of the present invention.

FIGS. 12 to 14 show states where the interlabial pad of which the length in the lateral direction of the body fluid storage layer 42 is longer than that of the labial following layer 44. FIG. 12 shows a state where a wearer with labia of average depth wears the interlabial pad of which the length in the lateral direction of the labial following layer 44g is especially short and is shorter than that of the body fluid storage layer 42g. Since the labial following layer 44g is especially short, at the labial inner wall there are parts, which are not in contact with this labial following layer 44g. On the other hand, since the body fluid storage layer 42g has a normal length, it slightly protrudes from between the interlabia, and a space 43g is brought about at parts where the labial inner wall is not in contact with the labial following layer 44g.

FIG. 13 shows a state where a wearer with slightly shallow labia wears the interlabial pad of which the length in the lateral direction of the body fluid storage layer 42h is especially long and is longer than that of the labial following layer 44h and the total length of the labial inner wall. The labial inner wall is in contact with the labial following layer 44h, however, at just the outside thereof, a space 43h is brought about between the body fluid storage layer 42h of the extending area and the wearer's body.

FIG. 14 shows a state where a wearer with slightly deep labia wears the interlabial pad of which the length in the lateral direction of the labial following layer 44i is shorter than that of the body fluid storage layer 42i. Since the labial following layer 44i is especially short, at the labial inner wall there are parts, which are not in contact with the labial following layer 44i, and a space 43i is brought about between the body fluid storage layer 42i and the wearer's body.

Figure 17:
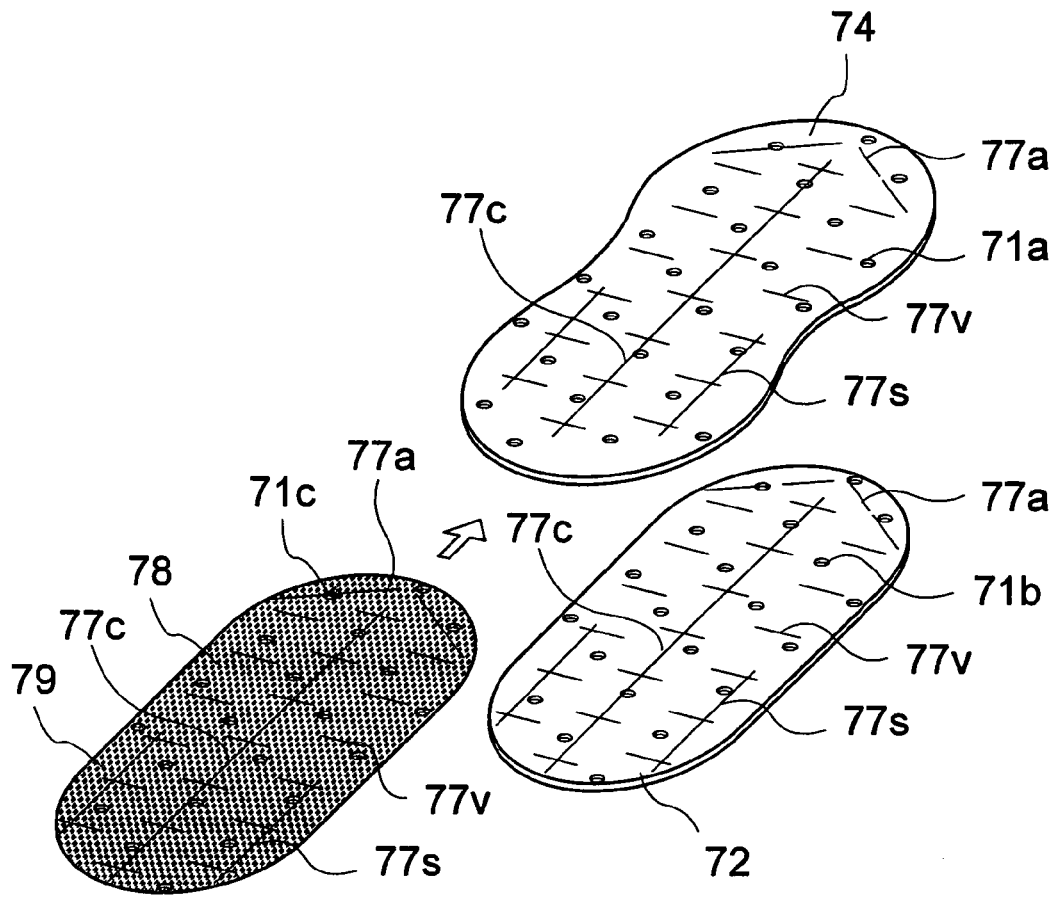
FIG. 17 is a developed view of the interlabial pad of the present invention.
Figure 18:
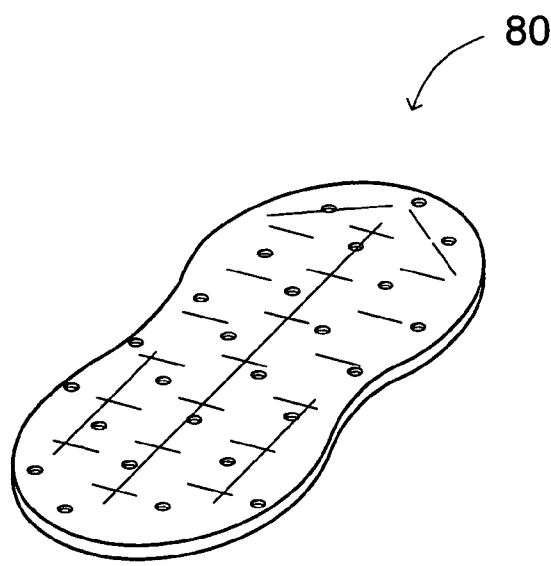
FIG. 18 is a view showing an absorbent body of the interlabial pad of the present invention.

FIGS. 17 to 20 show the interlabial pad 100 where the completed article has a sectional view as in FIG. 8 is shown by parts and is manufactured in stages. FIG. 17 shows a state where the absorbent body is formed by attaching the labial following layer 74 and the body fluid storage layer 72. The slit 77a which diagonally extends at the front, the slit 77c which extends at the longitudinal center part, the slit 77s which extends longitudinally at the part extending to the extending area, and the slit 77v which extends in the right-and-left direction or in the lateral direction are formed at the labial following layer 74, the body fluid storage layer 72 and the diffusion layer 78. Also, some dimples 71a by embossing are formed. Some dimples 71b by embossing are formed on the body fluid storage layer 72. The diffusion layer 78 can be positioned as an option between the labial following layer 74 and the body fluid storage layer 72. That is, as the interlabial pad, examples can include those in which the diffusion layer 78 is sandwiched between the labial following layer 74 and the body fluid storage layer 72 and those where it is not sandwiched. Since it becomes easier to widely absorb menstrual blood at the body fluid storage layer 72, it is more preferable to have the diffusion layer 78. There are dimples 71c on the diffusion layer 78, and the substrate thereof is mesh, and mesh holes 79 are widely distributed. Those parts constitute an absorbent body 80 shown in FIG. 18.

Figure 19:
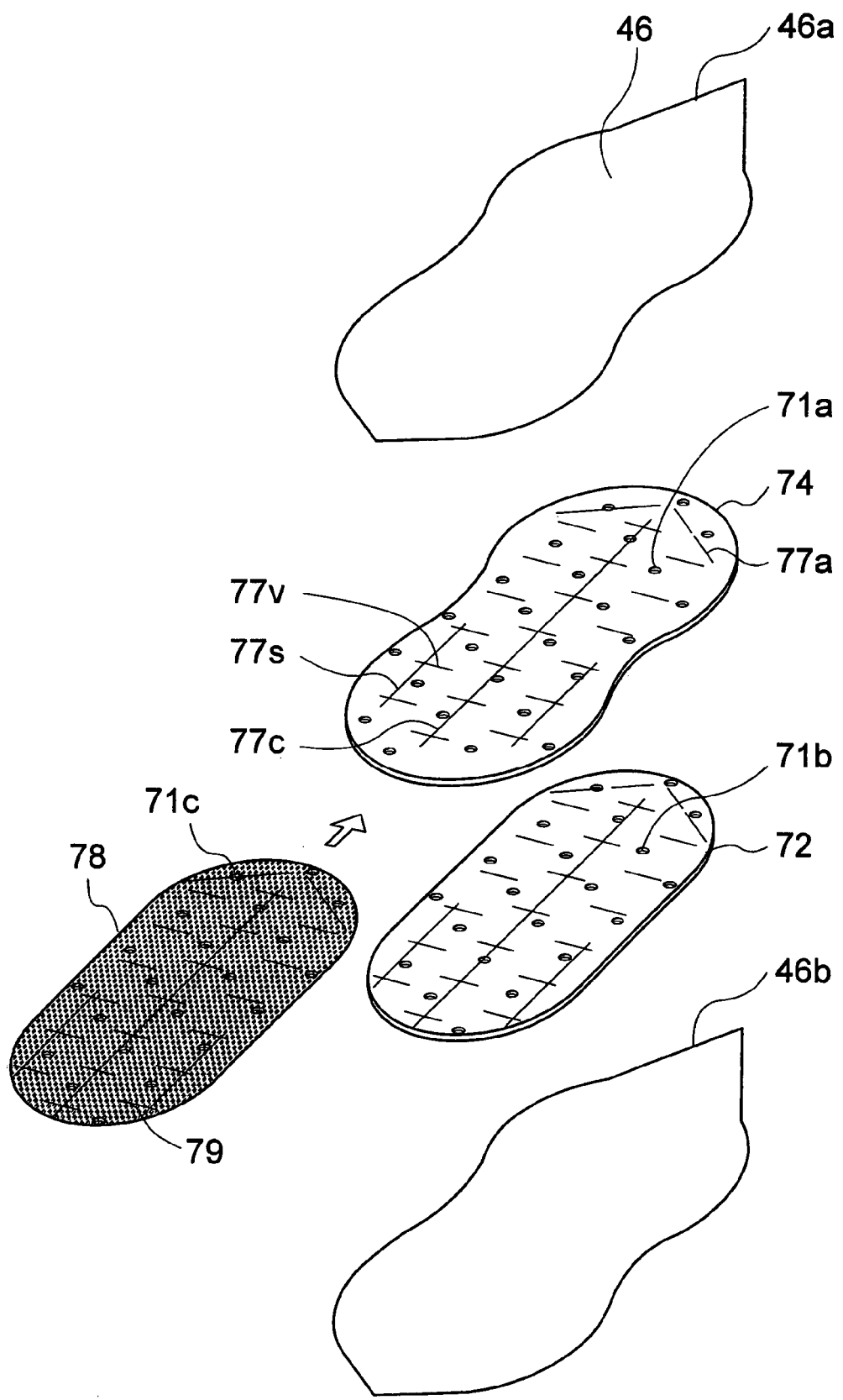
FIG. 19 is a developed view of an absorbent body of the interlabial pad of the present invention.

FIG. 19 shows a state where formed is an interlabial pad or an intermediate thereof comprising the surface side sheet 46a and the back face side sheet 46b of the covering material 46. The interlabial pad or the intermediate thereof is made up of one in which the surface side sheet 46a, the labial following layer 74, the body fluid storage layer 72 and the back face side sheet 46b are laminated in this order or one where the surface side sheet 46a, the labial following layer 74, the body fluid storage layer 72, the diffusion layer 78 and the back face side sheet 46b are laminated in this order.

Because the labial following layer 74, the body fluid storage layer 72 and the diffusion layer 78 are the same as described above they are omitted here. Material qualities of the surface side sheet 46a and the back face side sheet 46b which are components of the covering material and other parts are described below. These components can be integrally fabricated, and joined at the peripheral parts by a hot melt to form the interlabial pad and the intermediate thereof.

Figure 20A:
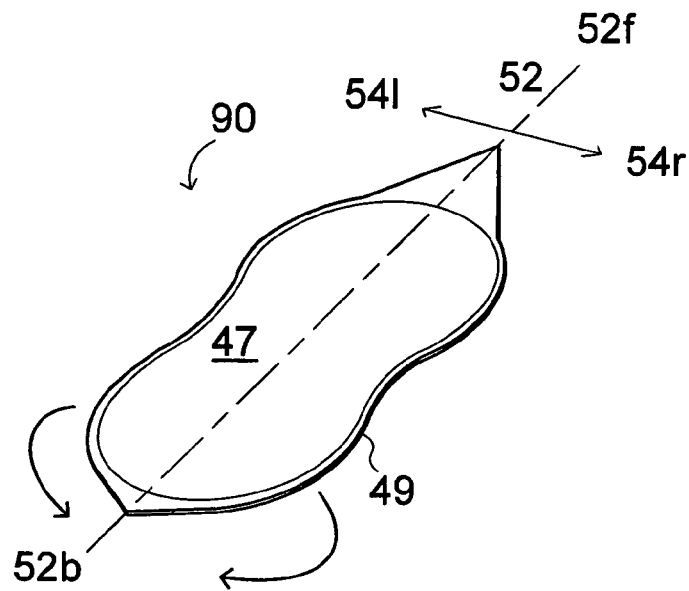
FIGS. 20A-20D are views showing a state where an assembly of the interlabial pad of the present invention is before being folded to attach a miniature sheet piece.
Figure 20B:
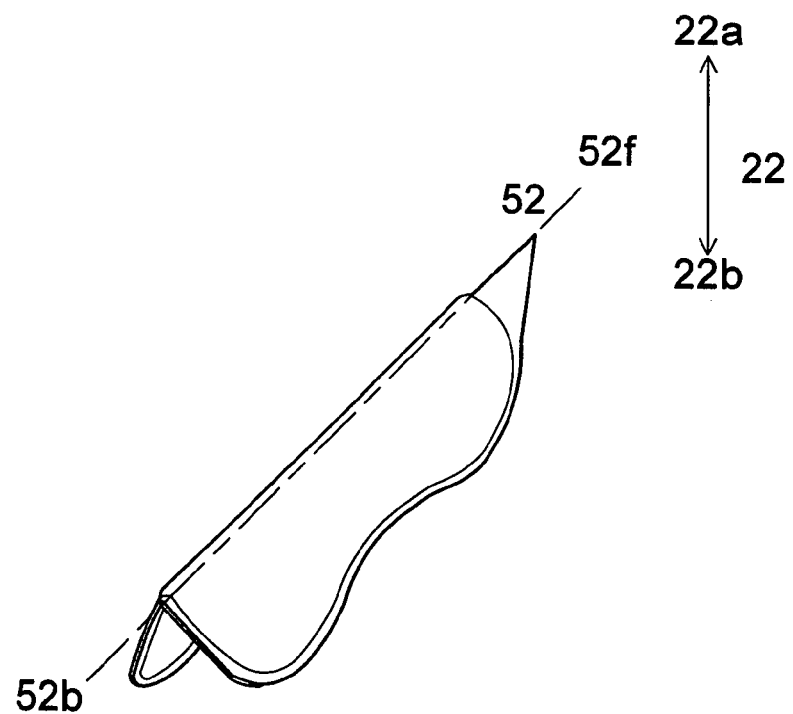
Figure 20C:
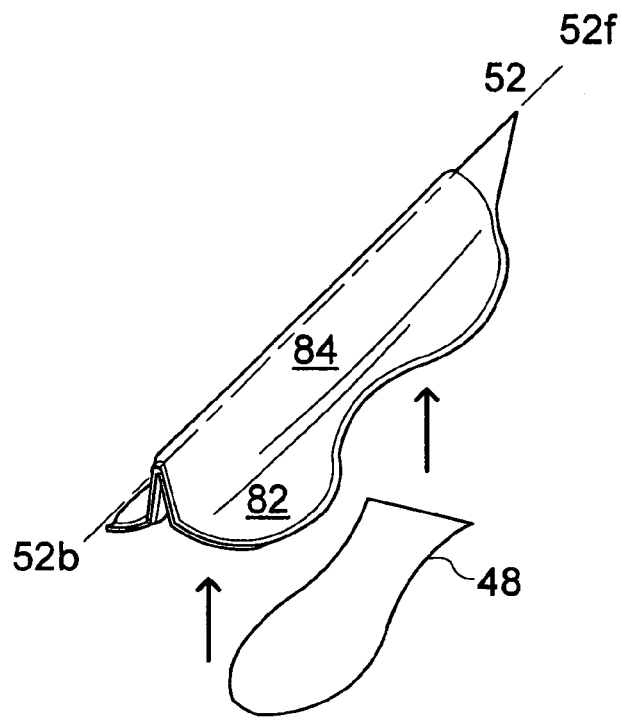
Figure 20D:
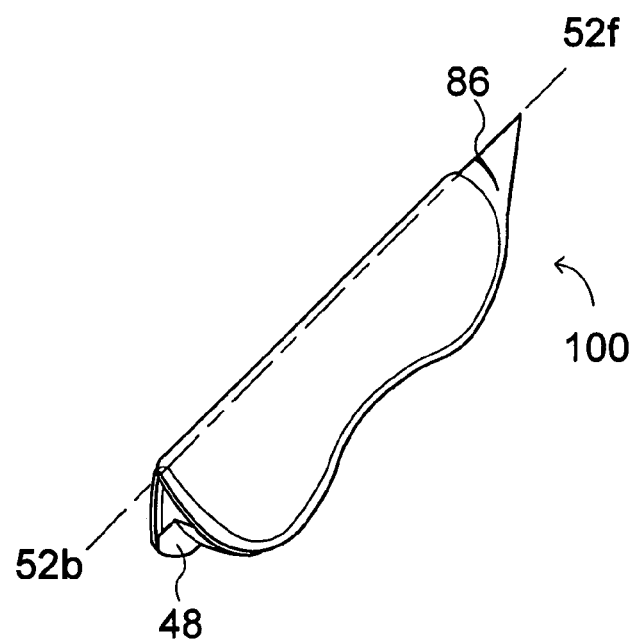

FIGS. 20A to 20D show a state where the completed interlabial pad 100 is formed by performing an additional processing such as folding to the formed interlabial pad or the intermediate thereof. In FIG. 20A, the interlabial pad or the intermediate 90 fabricated in FIG. 19 is depicted in conjunction with a folding axis 52 (52f is front and 52b is back) nearly along the longitudinal axis. The axis which intersects this axis is an axis which extends in the lateral direction of the interlabial pad or the intermediate 90, and can be called the right side 54r and the left side 54l. The interlabial pad or the intermediate 90 is joined at the side end parts 49 which correspond to the peripheral parts. The interlabial pad or the intermediate 90 is folded downward according to a curved arrow in the figure. At this time, the upper side face of the interlabial pad or the intermediate 90 thereof becomes the body side 22a. FIG. 20B shows a state where the interlabial pad or the intermediate 90 is folded along the folding axis 52 to become chevron. FIG. 20C shows a state where the interlabial pad or the intermediate 90 is folded back to form the extending area 82. The vicinity of the top part that retains a chevron shape the long convex area 84 is as shown in FIG. 6. The miniature sheet piece 48 is further attached at the base side face of the extending area 82 of the interlabial pad or the intermediate 90, which extends in this manner. This can stably retain the chevron shape of the long convex area 84. In the completed article 100 in FIG. 20D, shown is a state where the non-joint part of the miniature sheet piece 48 (part which is not in contact with the interlabial pad or the intermediate 90) is folded in at a line along the longitudinal axis and a fold back of the extending area 82 is recovered. Making such a form can make the completed article of the interlabial pad 100 compact, and it is preferable to perform individual or collective wrapping. Hereinafter, various aspects of the present invention are described in greater detail in conjunction with the materials and numerical values.

[Composition of the Absorbent Body]

In the interlabial pad of the present invention, the composition ratio of the apparent thickness in the "absorbent body" is set at 60/40 to 95/5 for the interlabial following layer/body fluid storage layer. For example, in FIG. 2, the labial following layer 44 and the body fluid storage layer 42 are overlapped, and the thickness of the interlabial pad 40 in a state fit between the interlabia is preferably from 2 to 20 mm and more preferably in a range of 4 to 10 mm. Especially when the thickness is less than 2 mm, the thickness becomes smaller (thinner) upon absorbing menstrual blood, and repulsion force which occurs against the labial interleaving force by the labia pudenda is decreased, thus there is a possibility that the interlabial pad falls from between the interlabia. On the other hand, when it is more than 20 mm, repulsion force which occurs against the interleaving force by the labia becomes too large, on the contrary, and the right-and-left labia are expanded, and thus not only a possibility that the interlabial pad falls is increased, but also a foreign feeling is also given to the wearer. Here, the apparent thickness which constitutes the absorbent body can be preferably set at preferably, the labial following layer/body fluid storage layer can be set at 60/40-95/5.

When the composition ratio of the apparent thickness is set at less than 60/40, the following property in response to behavioral changes of the labial inner wall is reduced or it becomes difficult to reduce a rigid feeling of the body fluid storage layer, and thus there is a possibility that a foreign feeling is given to the wearer. On the other hand, when it is set at more than 95/5, it is considered that it is difficult to transfer menstrual blood acquired at the labial following layer to the body fluid storage layer. It is considered that the labial following layer can be saturated sooner than the body fluid storage layer and that there is a case where menstrual blood leakage is induced without fully exploiting the maximum absorbent amount as the absorbent. Also, the apparent thickness of the absorbent body is preferably in a range of 2 to 20 mm. However, in the interlabial pad worn being folded (folded in about two) so that the covering materials at the garment side are opposed to one another nearly along the longitudinal direction centerline, the apparent thickness of absorbent body before being folded is preferably in a range of 1 to 10 mm. The apparent thickness can be measured without load at a state previously described where the cross sectional area is measured, i.e., a state where the absorbent body at a position in contact with the ostium vaginae in the longitudinal direction is cut in the lateral direction.

The absorbent body of the interlabial pad of the present invention, wherein the apparent density of the body fluid storage layer which constitutes the absorbent body is 0.02 g/cm$^3$ or more higher than that of the labial following layer, and the apparent density of the body fluid storage layer is set at 0.07 g/cm$^3$ or more. For example, when the difference in the apparent density of the body fluid storage layer and the labial following layer is less than 0.02 g/cm$^3$, since the density gradient of the labial following layer and the body fluid storage layer becomes reduced, there is a possibility that the difference in relative capillary force attributed, to surface tension is decreased and the flow of menstrual blood by the so-called capillary phenomenon is reduced. Therefore, when it becomes difficult to transfer menstrual blood acquired at the labial following layer to the body fluid storage layer, the labial following layer becomes a saturated condition before the body fluid storage layer becomes a saturated state, and tentatively, menstrual blood with a high rate and at a large amount which flows downward along the labial inner wall is discharged again, in the labial following layer which has been in a saturated state, power for absorbing menstrual blood from the labial inner wall is considerably reduced and it is considered that it becomes difficult to prevent outflow of menstrual blood by the absorption. A difference in the apparent density of the body fluid storage layer and the labial following layer is preferably in a range of 0.02 to 0.2 g/cm$^3$. The apparent density of the body fluid storage layer is preferably at least 0.07 g/cm$^3$ or more, and further more preferably in a range of 0.07 to 0.3 g/cm$^3$. For example, when the apparent density of the body fluid storage layer is less than 0.07 g/cm$^3$, since porosity which constitutes the body fluid storage layer is high, it is easily compressed, and thus there is a possibility that menstrual blood once absorbed and stored is released by deformation due to compression. On the other hand, when the apparent density of the body fluid storage layer is more than 0.3 g/cm$^3$, since the porosity which constitutes the body fluid storage layer is too small, it becomes difficult to absorb menstrual blood, and further there is a possibility that a rigid feeling is enhanced.

[Materials of the Covering Material]

Materials used for the absorbent body covered with the covering material can be the same as or different from those of the labial following layer and the body fluid storage layer. It is desirable that the labial following layer can be compressed and deformed more easily than the body fluid storage layer, and materials used are appropriately selected depending on the following characteristics. For example, the materials which constitute the labial following layer and/or the body fluid storage layer can be used without special distinction, and it is possible to use pulp, chemical pulp, rayon, acetate, natural cotton, and synthetic fibers alone or in mixture. Also, sheet materials can be used by processing into powder. For materials made into powder and granules, powdered individual materials are not interlocked with each other and flexibility is enhanced by being used for the labial following layer or the body fluid storage layer and these layers easily follow behavioral changes of the labia and the labial inner wall, and thus it becomes difficult to give a foreign feeling to the wearer. Also, cellulose foams and open foams of synthetic resins can be used as the absorbent body. By using foam for the labial following layer, the porosity is increased, a rigid feeling of the body fluid storage layer can be reduced in the labial following layer, the foam can be deformed and follow the morphological changes of the labial inner wall with less resistance, and therefore, it is more difficult to give a foreign feeling to the wearer. Additionally, in order to enhance the body fluid storage property of the body fluid storage layer, as materials used for the body fluid storage layer, particulate absorbent polymer and absorbent polymer fibers can be mixed. Also, in order to enhance the retention property of menstrual blood (or body fluid) by retaining height of the body fluid storage layer, chemical pulp, acetate and synthetic fibers crosslinked by a crosslinker and crimped can be mixed.

In the method for forming these materials into an absorbent body, it is preferable that the apparent thickness which constitutes the absorbent body is 60/40 or more for the labial following layer/body fluid storage layer, and it is preferable that the apparent density difference of the labial following layer and body fluid storage layer is 0.02 g/cm$^3$ or more.

Also, the absorbent body is not especially limited as long as the density of the body fluid storage layer is set to be high, and for example, a sheet made by the air laid method, melt blown method, spun lace method, and paper making method can be given. Moreover, in order to prevent losing shape in use, embossing can be performed by passing the sheet between rollers given dot or lattice patterning. Also, in order to prevent interlayer peeling between the labial following layer and the body fluid storage layer, the absorbent body can be integrated and molded by an adhesive and embossing. Specific examples of the integrated molding include, for example, embossing. In order to prevent losing shape in use and prevent the interlayer peeling between the labial following layer and the body fluid storage layer even in a wet state, preferably an emboss rate for the absorbent body area is in a range of 0.6 to 30%. In order to smoothly transfer menstrual blood absorbed at the labial following layer to the body fluid storage layer, it is preferable that the labial following layer and the body fluid storage layer are integrated without interlayer peeling while wearing, and thus it is preferable that the embossing is evenly conducted at the absorbent body.

In the absorbent body of the interlabial pad of the present invention, the labial following layer and the body fluid storage layer comprise a fibrous assembly, wherein the fiber length of the fibers which mainly constitutes the labial following layer is made up of fibers longer than the fiber length of the fibers which mainly constitutes the body fluid storage layer. When menstrual blood is absorbed, sometimes materials which constitute the absorbent body are drawn to one another by surface tension of menstrual blood, the distance between the materials is shortened, and the apparent thickness of the absorbent body is thinned. When the apparent thickness of the absorbent body and further the apparent thickness of the interlabial pad becomes thin, the repulsion force based on elasticity of the interlabial pad which resists the interleaving force of the labia is weakened, and therefore a possibility that the interlabial pad falls is increased. Also, since the apparent density is increased, a rigid feeling occurs in some cases. Therefore, it is preferable that the fiber length of the fibers which mainly constitute the labial following layer is longer than the fiber length of the fibers which mainly constitute the body fluid storage layer. By being made up of such fibers, even when the labial following layer absorbs menstrual blood, the labial following layer can be easily deformed. As one specific composition of the absorbent body, the labial following layer can be made up of fiber assembly in which rayon selected from a range of fineness of 1.1 to 4.4 dtx and fiber length of 20 to 51 mm at a mixing ratio of 60 to 90% and natural cotton at 40 to 10% are laminated. Also, the body fluid storage layer can be made up of fiber assembly in which fibers obtained by laminating pulp selected from a range with a fiber length of 1 to 10 mm at a mixing ratio of 80 to 99% and particulate absorbent polymer at 20 to 1% are made into a sheet by embossing. These labial following layer and body fluid storage layer can constitute an absorbent body having a total of 50 to 450 g/m$^2$ by specific weight per unit and a total apparent thickness of 2 to 20 mm. It is preferable that the relative composition ratio of apparent thickness of the labial following layer to that of the body fluid storage layer is in a range of 60/40 to 95/5. Also, the apparent thickness of the labial following layer is 1.0 to 14 mm, and the apparent thickness of the body fluid storage layer is preferably in a range of 0.6 to 6 mm. Moreover, for "major," when the same substance shows a weight of 60% or more based on a weight of each layer, the substance can be referred to as a major substance.

An index which indicates that the labial following layer is compressed and deformed more easily than the body fluid storage layer includes "KES compression property." The following includes a specific example. The labial following layer was made up of rayon with a fineness of 3.3 dtx and fiber length of 51 mm at the mixing ratio of 85% and natural cotton at 15%, laminated at 180 g/m$^2$ by specific weight per unit, and the apparent thickness was set at 2.5 mm. The body fluid storage layer was made up of pulp with a fiber length of 2 to 5 mm at 100%, laminated at 80 g/m$^2$ by specific weight per unit, and the apparent thickness was set at 1.0 mm. A test piece (5 cm×5 cm) of each layer was placed on a test table, and compressed by a copper plate with a circular plane of compression area 2 cm$^2$ at a velocity of 50 mm/second up to the maximum load of 4900 Pa. The compression rigidity (LC) represents linearity of a compression property, the higher the value is, the higher the rigidity against compression is. The test piece of said each layer showed 0.32 and that of the body fluid storage layer showed 0.41. In this regard, the labial following layer can be compressed and deformed more easily than the body fluid storage layer even when the absorbent body becomes a wet state, and thus it is possible to retain the following property in response to the labial inner wall and to reduce a rigid feeling of the body fluid storage layer by the labial following layer. The wet state shown here indicates a state up to less than the maximum absorbent amount of each layer.

Also, for example, excess body pressure is given between the interlabia by sitting on a chair, or less body pressure is given between the interlabia by maintaining a standing posture, and thus high or low inner pressure repeatedly occurs between the interlabia in response to a body balance change of the wearer. Thus, in the absorbent body of the interlabial pad, it is preferable that a foreign feeling is not given to the wearer by being compressed with less pressure when the body pressure is given and the thickness is recovered when the body pressure is released, thereby falling off of the interlabial pad can be prevented. That is, it is preferable that the absorbent body of the interlabial pad is compressed with less resistance and exhibits a high recovery rate of thickness, and it is more preferable that the labial following layer opposed to the labial inner wall has the above function. Recovering character (RC) in the compression property represents resilience of the compression property, and the higher its value is, the higher the recovery rate for the compression is. In the example of the present invention, the test piece of the labial following layer showed 46% and the test piece of the body fluid storage layer showed 28%.

By resilience of the compression property, the labial following layer reduces a rigid feeling of the body fluid storage layer and does not give a foreign feeling to the wearer. Additionally, the high recovery rate of the thickness prevents the falling off of the interlabial pad. In order to give the following property in response to the labial behavior and to make it difficult to give a foreign feeling to the wearer, it is preferable to reduce flexural rigidity of the absorbent body and to give flexibility, a reduction of flexural rigidity is obtained by giving a rigidity difference by performing embossing or slit processing to the body fluid storage layer. Here, in consideration of texture to the skin, performing the slit processing in which a stiffness difference is obtained by segmenting fiber entanglement is more preferable than embossing where the stiffness difference is obtained by a density difference. Slit processing can be those which extend in the lateral direction in a broken line and are disposed in a cross-woven pattern in the longitudinal direction, and includes the slit processing performed by a slit blade with a length of 10 mm. Also, when fibers are laminated, by making the orientation of fibers used random, a rigid feeling due to the orientation of fibers per se can be reduced and flexibility of the absorbent body can be enhanced. Examples include a process of conveying so that it is difficult to give tensile force to the absorbent body after laminating fibers. An index of the fiber direct orientation includes a ratio of the maximum tensile strength in the longitudinal direction, i.e., a value obtained by dividing the tensile strength in the longitudinal direction by the maximum tensile strength in the lateral direction, of the absorbent body where embossing is performed for the fiber assembly where the fibers are laminated by rollers having each flat faces, is 40 or less.

In the absorbent body of the interlabial pad of the present invention, it is possible that it be characterized wherein at the body side of the body fluid storage layer, the diffusion layer is disposed at the position adjacent to the labial following layer and that the Klemm water absorbency of the diffusion layer in the longitudinal direction is made higher. Discharge pathways of menstrual blood from the ostium vaginae are broadly classified into three; a pathway of being retained in the vicinity of the ostium vaginae (pathway 1); a pathway of flowing along the cross direction (longitudinal direction) by wettability due to mucosa and mucilage at the vestibule or the labial inner wall (pathway 2); and a pathway of flowing in the downward direction along the labial inner wall (pathway 3). However, it is considered that since the discharge rate is high and the amount is large in pathway 3, menstrual blood is discharged in the right-and-left direction (lateral direction). Since the shape of a woman's labia is nearly right-and-left symmetrical and longitudinal, it is preferable that the whole shape of the interlabial pad is also a substantially longitudinal shape. When menstrual blood is discharged frequently at a large amount in the above pathway 3, the maximum absorbent amount can also be exploited at the body fluid storage layer and the labial following layer in the right-and-left areas of the interlabial pad, and thus it is possible to prevent menstrual blood outflow.

[Materials of the Diffusion Layer]

As materials used for the diffusion layer, desirable are those where the Klemm water absorbency in the longitudinal direction is higher than that in the labial following layer, if so, materials are not especially limited, however, it is possible to use any of natural and chemical fibers. For example, natural fibers include celluloses such as pulverized pulp and cotton. Examples of chemical fibers include regenerated celluloses such as rayon and fibril rayon, semi-synthetic celluloses such as acetate and triacetate, those in which a hydrophilic treatment is given to thermoplastic hydrophobic chemical fibers. The above-mentioned thermoplastic hydrophobic chemical fibers include filaments such as polyethylene, polypropylene, and polyethylene terephthalate or composite fibers where the core part is of polypropylene or polyethylene terephthalate and a sheath part is of polyethylene. When the material is made into a sheet, included are woven fabric and nonwoven fabric. Especially in the case of nonwoven materials, web forming can be performed using dry forming methods (card method, spun bonding method, melt blown method, air laid method, etc.) and wet forming methods alone or in combination of two or more. Bonding methods include thermal bonding, needle punching and chemical bonding, etc., and are not especially limited thereto. Also, spun lace where the sheet is formed into a sheet by hydroentanglement can be used.

As a specific composition of the diffusion layer, it is preferable to select spun lace nonwoven fabric with 20 to 50 g/cm$^2$ by specific weight per unit and thickness of 0.2 to 1.0 mm obtained by entangling the rayon 100% fibers with a fineness of 1.1 to 4.4 dtx and fiber length of 25 to 51 mm by water flow, and making a spun mesh pattern. The Klemm water absorbency in the longitudinal direction is specifically described. The labial following layer was made up of rayon with a fineness of 3.3 dtx and fiber length of 51 mm at a mixing ratio of 85% and natural cotton at 15%, is laminated at 180 g/m$^2$ by specific weight per unit, and made into a sheet by embossing so as to become a height of 2.5 mm. The diffusion layer is the spun lace made up of 100% rayon with a fineness of 1.4 dtx and fiber length of 44 mm, laminated at 25 g/m$^2$ by specific weight per unit so as to become a thickness of 0.28 mm and made into a sheet by a mesh pattern where meshes with a diameter of 1 mm are disposed in a cross-woven pattern by the hydroentanglement method. The labial following layer and the diffusion layer were soaked in artificial menstrual blood made by Uni-Charm Corporation, and the Klemm water absorbency in the longitudinal direction was measured after 10 min. It was 41 mm at the labial following layer whereas it was 50 mm at the diffusion layer. Here, the evaluation method of Klemm water absorbency and the method for making the artificial menstrual blood are described in detail below.

In materials used for the diffusion layer, in order to make the diffusion area of menstrual blood direct toward the longitudinal direction, menstrual blood diffusion in the lateral direction is segmented by performing slit processing directed in the longitudinal direction. Menstrual blood is led in the disposing direction of the fibers by directing the orientation of fibers in the longitudinal direction, or menstrual blood is led in the longitudinal direction by a capillary phenomenon by performing embossing which imparts a high density area which extends in the longitudinal direction. However, if the orientation of fibers is directed in the longitudinal direction or if the embossing is performed, a rigid feeling of the diffusion layer is enhanced. Therefore, more preferable examples include materials in which the slit processing directed in the longitudinal direction is performed for spun lace nonwoven fabric given a mesh pattern by water flow. By using mesh spun lace nonwoven fabric, an interfiber distance becomes small at the area between openings and thus the capillary force is enhanced, further by slit processing, the Klemm water absorbency in the longitudinal direction is further increased, and additionally since the opening parts can be easily deformed, flexibility at the diffusion layer is also enhanced, and it becomes difficult to inhibit the labial following layer from being deformed easily.

The dimensions of the diffusion layer are not especially limited, however, in order to easily exploit the maximum absorbent amount of the body fluid storage layer at the front and rear areas, it is preferable that the dimension of the diffusion layer in the longitudinal direction is larger than that of the body fluid storage layer. First as a specific composition of an absorbent body, for example, included is an absorbent body wherein the labial following layer is laminated at a mixture ratio of 60 to 90% of rayon selected from a range with a fineness of 1.1 to 4.4 dtx and fiber length of 20 to 51 mm and at 40 to 10% of natural cotton, in the body fluid storage layer, the mixture of pulp selected from a range with a fiber length of 1 to 10 mm at 80 to 99% and particulate super absorbent polymer at 20 to 1% is laminated, the resultant fibers are made into a sheet by embossing, and which has a total of 50 to 450 g/m$^2$ by specific weight per unit and a total apparent thickness of 2 to 20 mm. When producing the above absorbent body composition, since pulp with a fiber length of 1 to 5 mm is mainly used, there is a possibility that the productivity is deteriorated by dropping off the pulp in conveyance or making the pulp adhere to an emboss roller by embossing. In order to prevent deterioration in productivity, the whole area of the absorbent body at the garment side of the body fluid storage layer can be covered with the covering material. The covering material is not especially limited as long as the pulp does not drop in conveying and does not inhibit a barrier property from adhering to the roller and the flexibility of the whole interlabial pad, however, preferred are materials used in the absorbent body previously described in order to further enhance the maximum absorbent amount. Specifically, examples include tissue set at 15 g/m$^2$.

Therefore, as a more suitable specific example of the labial following layer, the body fluid storage layer and the diffusion layer, the garment side of the body fluid storage layer can be covered with tissue of 10 to 20 g/m$^2$, the pulp selected from a range with a fiber length of 1 to 10 mm is laminated at 60-120 g/m$^2$ in the body fluid storage layer thereon, the spun mesh lace of rayon with a fineness of 1.1 to 4.4 dtx and fiber length of 25 to 51 mm is laid down at the diffusion layer at the body side of the body fluid storage layer, rayon selected from a range with a fineness of 1.1 to 4.4 dtx and fiber length of 20 to 51 mm at a mixture ratio of 60 to 90% and natural cotton at 40 to 10% are laminated at 150 to 250 g/m$^2$, and these materials can be made into a sheet by dot embossing. The apparent thickness of the labial following layer is preferably from 10 to 14 mm, and the apparent thickness of the body fluid storage layer is preferably in a range of 0.6 to 6.0 mm.

[Covering Material]

The interlabial pad of the present invention comprising, an absorbent layer in which the water permeable surface side sheet faced to the body side and the water permeable or impermeable back face side sheet faced to the garment side are joined for covering the absorbent body which absorbs the body fluid, said absorbent layer is made up of a long convex area which forms the top part directed to the body side by being folded nearly along the longitudinal direction centerline so that the back face side sheets are opposed to one another and the extending area formed being extended from the both side parts of said long convex area to the lateral direction, wherein the body fluid storage layer is positioned at the long convex area. The body fluid storage layer of the absorbent body is positioned at the long convex area which is fit between the interlabia, therefore, menstrual blood acquired at the labial following layer can be transferred to the body fluid storage layer in no time, and thus it is possible to prevent the outflow of menstrual blood without allowing only the labial following layer to saturate. Also, the body fluid storage layer is not installed at both side parts of the extending area, therefore, it becomes difficult that the combined pad or the garment is in contact with both side parts of the body fluid storage layer, and thus it is possible to prevent the outflow of menstrual blood from the right-and-left directions of the interlabial pad to the combined pad or the garment. Furthermore, the labial following layer extends to the extending area, therefore, the adhesive areas of the labial following layer not only to the labial inner wall but also to the pudendum are increased, and thus it is possible to prevent leakage of menstrual blood. The body fluid storage layer can be positioned in the long convex area by the part thereof, and is not limited thereto. It is preferable that the body fluid storage layer is not positioned at the area along the centerline which extends in the longitudinal direction. It is considered that the density of the body fluid storage layer is set to be high, therefore, when it is positioned at the position opposed to the vestibule, a rigid feeling of the body fluid storage layer is given to the wearer when positioning the body such as when sitting on a chair, and thus it becomes easy to give a foreign feeling.

Also, by making a finger contact in the vicinity of the longitudinal direction centerline at the garment side of the interlabial pad while wearing between the interlabia, therefore, the interlabial pad can be reliably worn because the stiffness of the finger can push and open the labia, and thus it becomes possible that no space is brought about between the vestibule or the labial inner wall and the body side of the interlabial pad. A finger insertion opening capable of securing a finger in the longitudinal direction of the back face side sheet can be formed, by providing a miniature sheet piece where one or more joint parts at the both sides of the longitudinal direction of the garment side of the back face side sheet and one or more non-joint parts at the lateral direction of the back face side sheet are joined. In the interlabial pad which comprises the miniature sheet piece having the finger insertion opening at the garment side, the finger is inserted so that the fingerprint surface of the finger is in contact with the back face side sheet, therefore, the position of the ostium vaginae which is the concave part can be detected with a fingertip excellent in sensitivity, and thus it becomes possible to wear the interlabial pad at a definite position. Therefore, since the wearing becomes reliable, it is possible to further prevent leakage of menstrual blood. The shape of the interlabial absorbent layer is not especially limited as long as it is a shape capable of being placed between a woman's interlabia comfortably. The shape is not limited, as long as it is a form, which fits a woman's labia area such as oval, gourd and droplet shapes.

[Water Permeable Sheet]

For the water permeable sheet positioned at the body side of the interlabial pad, used are materials, which are liquid, hydrophilic and are not irritative to the skin. Such materials of nonwoven fabric obtained by the production method such as melt blown, spun bonding, point bonding, through air, point bonding, needle punching, wet forming, wet forming spun lace, and foam film methods alone or in composite thereof are used.

Fibrous sheets include sheets where rayon, acetate, cotton, pulp or synthetic resin is rendered the ingredient, fibers are made from the ingredient alone or in composite to make a core sheath structure, and the fibers alone or in mixture are made into a sheet.

Among such materials, in consideration of liquid mobility from the interlabial inner wall and chemical irritation by surface active agents, the spun lace nonwoven fabric is preferable for fibers where natural cotton at 5 to 30% and rayon or acetate at 70 to 95% are mixed are adjusted in a range of 20 to 50 g/m$^2$, subsequently the fibers are entangled with one another by hydroentanglement and dried, the thickness is adjusted in a range of 0.3 to 1.0 mm. The yarn quality used at this time is selected in a range of 15 to 60 mm for natural cotton, in a range of 25 to 51 mm and a range of 2.2 to 6.6 dtex for rayon or acetate.

[Water Impermeable Sheet]

As materials of the water impermeable sheet used for the interlabial sheet, it is possible to use those capable of preventing menstrual blood retained in the absorbent body from leaking out of the interlabial pad. Also, by using the moisture permeable materials, moisture dumpiness can be reduced while wearing, and it becomes possible to reduce discomfort while wearing.

As such materials, it is possible to use, for example, sheet film where the synthetic resin is made into film, aeration film obtained by filling an organic filler and performing a drawing treatment, laminated matter where paper, nonwoven fabric and film are laminated, aeration liquid blocking sheet having 10 to 30% openings obtained by positioning capillary tubes with a pore diameter in a range of 0.1 to 0.6 mm to direct to the absorbent body, and the like.

Furthermore, in consideration of the flexibility which does not impair the wearing feeling, it is preferable to use the film obtained from a range of 15 to 30 g/m$^2$ by specific weight per unit where low density polyethylene (LDPE) resin with a density of 0.900 to 0.925 g/cm$^3$ is a major ingredient.

[Miniature Sheet Piece]

For the miniature sheet piece, it is also possible to use the same materials as those for the above water permeable sheet and water impermeable sheet, however, it is preferable to use those having extensity or elasticity in the lateral direction.

By using such materials for the miniature sheet piece, even when the fingertip size of the wearer is larger than that of the set finger insertion opening, the miniature sheet piece extends to the right-and-left direction depending on the finger size, and thus it is possible to effectively utilize the interlabial pad according to the present invention regardless of the fingertip size of the wearer.

As materials originally having elasticity, included are, for example, synthetic rubber such as styrene-butadiene-styrene copolymer (SBS), styrene-isoprene-styrene block-copolymer (SIS), and urethane, film of which the raw material is an amorphous olefin type resin selected from a density of 0.88 to 0.900 g/cm$^3$, opening foam film, nets and the like. Also, it is possible to use a woven fabric or a texture in which fiber spinning filaments of which the raw material synthetic rubbers are woven. Furthermore, it is also possible to use spun bonding nonwoven fabric and melt blown nonwoven fabric of which the major ingredient is synthetic rubber, and effervescent foam sheet.

In consideration of a flexible texture while wearing, suitable materials include opening foam film of which the thickness is adjusted at 15 to 40 μm, the pore area is 0.28 to 1.77 mm$^2$ and porosity is 40 to 70%, and the raw material is SBS.

The nonwoven fabrics include spun lace nonwoven fabrics of which the raw material is composite synthetic fibers such as polyethylene (PE)/polypropylene (PP), PE/polyethylene terephthalate (PET), and PP/PP having thermal contractility in which the core and sheath ingredients are made up of high and low melting point ingredients, respectively, and the fibers are entangled by water flow pressure; shrink type nonwoven fabrics where the shrink of fibers is facilitated by giving re-hot air treatment; and so-called extensive spun bond in which continuous fibers are made into a sheet by thermal sealing and then tentering is forcibly performed in the vertical direction.

More specifically, as for flexibility, suitable materials with a rich drape feeling, included is the shrink type nonwoven fabric of which the raw material is composite synthetic fibers such as PE/PP, PE/PET and PP/PP with thickness of 2.2 to 6.6 dtex and length of 38 to 51 mm having thermal contractility in which the core and sheath ingredients are made up of high and low melting point ingredients, respectively, and the specific weight per unit is adjusted in a range of 20 to 60 g/m$^2$. And also, it is possible to use the laminated matter of the above materials.

When non-extensive materials are used by imparting the extensity, among the nonwoven fabrics, included are materials comprising separate or combining opening foam film, films of which the major ingredient is PE resin in addition to through air nonwoven fabric with a rich height bulky feeling treated by hot air, of which the raw material is said composite synthetic fibers such as PE/PP, PE/PET and PP/PP having thermal contractility in which the core and sheath ingredients are made up of high and low melting point ingredients, respectively; spun lace nonwoven fabrics where the fibers are entangled with water flow pressure; spun bond nonwoven fabrics where continuous fibers are laminated and made into a sheet; needle punch nonwoven fabrics in which the fibers are entangled by needles; and SMS nonwoven fabrics in which spun bond and melt blown are laminated in multiple layers and made into sheets.

Also, it is possible to impart the extensity by corrugated processing where the materials as described above are fit between male and female dies and the shape is embossed by heat, temperature and pressure. More specifically, included are those where the corrugated processing is given to the through air nonwoven fabric where the composite synthetic fiber adjusted in a range of thickness of 2.2 to 4.4 dtex and 20 to 60 g/m$^2$ by specific weight per unit is the major ingredient, to be capable of extending in the horizontal direction. In the corrugated processing, extensibility is at least 10% or more, more preferably, the disposition of the male and female dies is installed to make it possible to extend in a range of 20 to 50%, and more preferably, it is desirable to have behavior in a range of a load of 0.01 to 0.05 N/25 mm at 30% extension (test condition: by Tensilon tensile tester, velocity 100 mm/min, chuck interval 100 mm).

As another method for imparting the extensity, it is possible to use the methods such as cutting lines and cutting out into a circular shape.

[Composition of Interlabial Pad to which Biodegradability, Water Dispersibility and Water Solubility are Imparted]

It is preferable that the interlabial pad of the present invention is made up of biodegradable materials and/or water dispersible materials and/or water soluble materials. Such an interlabial pad can be dropped into a toilet bowl and flushed, therefore, disposal of the pad can be carried out simply and cleanly, and reduction of waste in a toilet can also be promoted.

Herein "biodegradability" is referred to as being decomposed to gas such as carbon dioxide and methane, water and biomass under an anaerobic or aerobic condition according to processes of the natural world in the presence of bacteria such as actinomycetes and other microorganisms, and being that the biodegradable ability of the substance (biodegradable rate, biodegradable degree) is comparative to naturally generating materials such as fallen leaves or synthetic polymers generally recognized to be biodegradable under the same environment. "Water dispersibility" means the same as water degradability, and refers to the characteristics of dissolving in large amounts of water or water flow, the fibers are easily dispersed into tiny pieces which do not obstruct common toilet piping although no effect is caused in a limited amount of moisture (menstrual blood) while wearing. "Water solubility" refers to the characteristics of dissolving in large amounts of water or water flow although no effect is caused in a limited amount of moisture (menstrual blood) while wearing.

<Water Permeable Sheet>

As materials which can be used for water permeable sheets, it is possible to use wet forming spun lace nonwoven fabrics selected from a range of fiber length of 1 to 15 mm in addition to the spun lace nonwoven fabrics. As other materials, it is possible to use biodegradable resins by hydrolysis such as poly lactic acid and polybutylene succinate. For example, included are melt blown nonwoven fabrics adjusted in a range of 20 to 60 g/m$^2$ by specific weight per unit and spun bonding nonwoven fabrics adjusted in a range of 15 to 30 g/m$^2$ by specific weight per unit and fiber thickness of 1.1 to 3.3 dtex, which are made from poly lactic acid. Moreover, an opening treatment can be given or my not be given to each nonwoven material.

As other material, it is possible to use tow which is continuous fibers of acetate or synthetic fiber alone or the laminate thereof by adjusting in a range of 50 to 300 g/m$^2$ by specific weight per unit and fibrillating fibers with one another.

<Absorbent Body>

As materials which can be used for the absorbent body, it is possible to use a nonwoven sheet obtained by needling. Moreover, in consideration of biodegradability of absorbent polymer materials, it is preferable to use carboxymethylcellulose fibers.

<Water Impermeable Sheet>

As the materials which can be used for the water impermeable sheet, it is possible to use polyvinyl alcohol (PVA) film, a film sheet where water-repellent treatment with silicone is given to one face or both faces or a part of PVA film, PVA film where silicone is mixed, starch film, films where biodegradable resins by hydrolysis such as poly lactic acid or polybutylene succinate are raw materials, and laminate paper such as tissue. Coloration can be given by mixing inorganic dyes in a range of 0.1 to 5% if necessary. In consideration of maintenance of anti-leakage under an excessive wet state and that an excessive load is not given to a septic tank, suitable is laminate paper where film with a thickness of 10 to 20 μm and where poly lactic acid is the raw material is laminated with the tissue selected from a range of 15 to 20 g/m² by specific weight per unit and further an attached area rate is given in a range of 5 to 40% upon laminating.

<Miniature Sheet Piece>

As materials which can be used for the miniature sheet piece, included are films where biodegradable materials such as poly lactic acid and polybutylene succinate are raw materials, films where water soluble materials such as spun bonding nonwoven fabric, melt blown nonwoven fabric, or PVA, carboxymethylcellulose (CMC) are raw materials, water dispersible tissues where nonwoven fabrics, cellulose fibers, regenerated cellulose fibers are major ingredients, and spun lace nonwoven fabrics.

Suitably, it is spun bonding nonwoven fabric or melt blown nonwoven fabric, and sheet adjusted in a range of thickness of 0.1. to 3.3 dtex and 15 to 40 g/m² by specific weight per unit, and is obtained by giving the above mechanical corrugated processing.

<Joining Method>

As a joining method, it is possible to use adhesion by polyvinyl alcohol having water solubility or water swelling property, bonding by heat sealing or hydrogen bond, separate or in appropriate combination thereof.

<Measurement of Maximum Absorbent Amount>

The maximum absorbent amount of the absorbent body can be measured by the following method. As measurement instruments, prepared are a balance, stop watch, plastic vessel and artificial menstrual blood. As artificial menstrual blood, used are the first grade reagents manufactured by Wako Pure Chemical Industries Ltd., and edible dyes manufactured by Koyo Products Co. Ltd., shown in Table 1.

| Reagent for artificial menstrual blood (values for one liter of ion-exchange water) | |
|---|---|
| (1) Sodium carboxymethylcellulose (NaCMC): (Wako first grade, 39-01335) | 8 g |
| (2) Glycerine (Wako first grade, 072-00621) | 80 g |
| (3) Sodium chloride (NaCl) (Wako first grade) | 10 g |
| (4) Sodium hydrogen carbonate (NaHCO₃) (Wako first grade) | 4 g |

-continued

| Edible dyes (Koyo Products)] | |
|---|---|
| (1) Red No. 102 | 8 g |
| (2) Red No. 2 | 80 g |
| (3) Yellow No. 5 | 10 g |

As the measurement instruments, used were a stirrer (manufactured by Yamato, LABO-STIRRER L-35), stopwatch, and viscometer (manufactured by Shibaura Systems Co. Ltd., Vismetron). For artificial blood, all portions were placed in the given vessel first mixing glycerine and sodium carboxymethylcellulose in small portions. Next, the ion-exchange water placed in a plastic vessel was added in small portions to the above mixture where sodium carboxymethylcellulose was mixed well with glycerine stirring by the stirrer. Sodium chloride and sodium hydrogen carbonate were added in small portions with further stirring. And, the mixture was mixed well until the reagents were thoroughly dispersed and, for example, was mixed for 3 hours at a maximum stirring speed. It was confirmed that the reagent was not left alone in the mixed mixture, and subsequently the edible dyes, 8 g of Red No. 102, 2 g of Red No. 2 and 2 g of Yellow No. 5 were poured at one liter of the ion-exchange water, and mixed for one hour at the maximum stirring speed. Subsequently, it was confirmed by the viscometer that the viscosity of this mixture was 22 to 26 mPa·s, and it was rendered artificial menstrual blood.

Next, test pieces were prepared. Samples in number N with a length of 100 mm were randomly collected in the longitudinal and lateral directions of the absorbent body. And the weight of the sample was measured by a balance (W1). The artificial menstrual blood previously prepared was placed in the plastic vessel at a depth of 10 mm or more. In this vessel, the collected test piece was set to be completely soaked in the artificial menstrual blood. And, it was left as is for 3 minutes (in the environment at this time, the temperature was 20° C. and humidity was 60%). After 3 minutes, the sample was taken out and the weight was measured by a balance (W2). The absorbent amount (maximum amount) was calculated by subtracting W1 from this W2 (W2−W1).

An absorption scale is obtained by dividing this absorbent amount by the weight of sample W1.

[Measurement of Klemm Water Absorbency]

In the measurement of Klemm water absorbency, liquid affinity (diffusivity) of the test piece is measured. As the measurement instruments, used were a ruler, stopwatch, plastic vessel, and the artificial menstrual blood obtained by the above method. Next the test pieces in the number N (N pieces) were randomly collected at a width of 25 mm and length of 100 mm in the longitudinal and lateral directions of the given sample. First, the artificial menstrual blood was placed in the plastic vessel at a depth of 10 mm or more.

The test piece was set to be soaked in the artificial menstrual blood at a depth of 5 mm from a front end of the test piece. This was left as is for 10 minutes (environment: temperature 20° C./humidity 60%). The artificial menstrual blood rose along the test piece, an absorbed distance on the test piece was measured from the surface of the artificial menstrual blood. The longer absorbed distance indicates the higher absorbency.

The following effects are anticipated in the interlabial pad with a shape capable of being placed between a woman's interlabia comfortably, comprising the absorbent body which absorbs body fluid and the covering material which covers the absorbent body, wherein the absorbent body is made up of the labial following layer located at the body side and the body fluid storage layer located downward thereof (garment side) of which the body side is covered with the labial following layer, the labial following layer is compressed and deformed more easily than the body fluid storage layer when the interlabial pad is worn, and the apparent density of the labial following layer is lower than that of the body fluid storage layer.

The labial following layer which is capable of being compressed and deformed more easily than the body fluid storage layer is positioned in the vicinity of the labial inner wall, therefore, even when the labia are inflected in the right-and-left direction along an axis in the vertical direction and the convex and concave shape of the labial inner wall is deformed, the labial following layer can be easily compressed and deformed in response to behavioral changes of the labial inner wall. Furthermore, it is difficult to give a foreign feeling to the wearer because the body side of the body fluid storage layer is covered with the labial following layer, and thus a rigid feeling of the body fluid storage layer can be simultaneously reduced by the labial following layer. Additionally, the body fluid storage layer is far more difficult to be compressed than the labial following layer and is located downward of the labial following layer, therefore, it is difficult to give the outside pressure to the body fluid storage layer, and thus it is prevented that menstrual blood leakage is induced by flowback of menstrual blood accumulated in the body fluid storage layer.

The labial following layer of which the density is set to be low is located in the vicinity of the labial inner wall and the body fluid storage layer of which the density is set to be high is located at the garment side thereof (lower face), therefore, menstrual blood in the discharge pathway flowing along the labial inner wall downward with a high flow rate and at a large amount is acquired by the labial following layer set at the lower density which is easily deformed and opposed in response to the behavioral changes of the vestibule and the labial inner wall and can be continued to be transferred to the body fluid storage layer by a capillary phenomenon between the labial following layer and the body fluid storage layer, and thus even when menstrual blood is discharged again, it is possible to acquire menstrual blood at the labial following layer and to prevent leakage of menstrual blood without allowing only the labial following layer to saturate. Simultaneously, menstrual blood is accumulated from the body fluid storage layer which is the garment side of the absorbent body, therefore, it is difficult that menstrual blood is retained on the surface of the interlabial pad, and thus, it is possible to prevent falls of the interlabial pad because the fluidity of menstrual blood can be inhibited.

What is claimed is:

1. An interlabial pad comprising:
   an absorbent body having a body fluid storage layer, a labial-following layer, and a diffusion layer positioned between the labial-following layer and the body fluid storage layer wherein a labial-following layer/body fluid storage layer composition ratio of an apparent thickness is between 60/40 and 95/5;
   a covering material having a water-permeable surface side sheet, for facing the labia of a wearer, and a back face side sheet, for facing the body fluid storage layer; and
   a side end portion, joining the surface side sheet with the back face side sheet,
   wherein at least a part of the labial-following layer is positioned between the surface side sheet and the diffusion layer, and the labial-following layer is adapted to deform together with the covering material in accordance with a labia shape of the wearer;
   the body fluid storage layer is in contact with the diffusion layer, and the diffusion layer is in contact with the labial-following layer to allow movement of body fluid from the labial-following layer to the body fluid storage layer;
   spaces are formed at both sides of the body fluid storage layer between the body fluid storage layer and the surface side sheet of the covering material, at least one of the spaces becoming smaller when the interlabial pad is folded in two along a folding axis so that the back face side sheet overlaps itself; and
   the labial-following layer is more flexible than the body fluid storage layer, wherein the garment side of the body fluid storage layer is covered with tissue having 10 to 20 g/m$^2$ specific weight per unit;
   a pulp selected from a range of fiber length of 1 to 10 mm is laminated at 60 to 120 g/m$^2$ by specific weight per unit in the body fluid storage layer on an upper face thereof;
   a mesh spun lace of rayon with a fiber length of 25 to 51 mm is laid down in the diffusion layer at a body side of the body fluid storage layer; and
   a mixture at a mixing ratio of 60 to 90% rayon selected from a range of a fiber length of 20 to 51 mm and 40 to 10% of natural cotton is laminated at 150 to 250 g/m$^2$ by specific weight per unit in the labial-following layer on an upper face thereof.

2. The interlabial pad according to claim 1, wherein the absorbent body has a size, weight and softness to be placed in and retained between the labia comfortably, and has a substantially longitudinal shape having longitudinal and lateral directions.

3. The interlabial pad according to claim 2,
   wherein the diffusion layer has a higher Klemm water absorbency than that of the labial-following layer in the longitudinal direction.

4. The interlabial pad according to claim 1, further comprising a folding axis that is substantially parallel to the longitudinal direction at about the center in the lateral direction, and the interlabial pad is retained to be placed between the labia of said wearer in a folded state at said folding axis.

5. The interlabial pad according to claim 2, wherein
   the labial-following layer and the body fluid storage layer expand in the longitudinal direction and the lateral direction;
   the labial-following layer and the body fluid storage layer are overlap; and
   the absorbent body is positioned so that the labial-following layer is in contact with the absorbent body side face of the covering material.

6. The interlabial pad according to claim 1,
   wherein an apparent density of the body fluid storage layer is greater than that of the labial-following layer.

7. The interlabial pad according to claim 1, wherein
   the labial-following layer comprises a first fibrous assembly;
   the body fluid storage layer comprises a second fibrous assembly;
   the first fibrous assembly comprises first fibers;
   the second fibrous assembly comprises second fibers; and
   the first fibers are longer than the second fibers.

8. The interlabial pad according to claim 4,
wherein said covering materiel comprises a surface side sheet and a back face side sheet;
said surface side sheet is water permeable;
said back face side sheet is water permeable or water impermeable;
said covering material comprises said absorbent body between said surface side sheet and said back face side sheet;
the interlabial pad further comprises a long convex area which forms a top part toward the body side of the wearer in a state where said surface side sheet extrudes from the surface by being folded along said folding axis so that the back face side sheets are opposed to each other;
an extending area which is extends from both sides of said long convex area in the lateral direction; and
said body fluid storage layer is positioned at the side of the back face side sheet closer than said labial-following layer, and a part of said body fluid storage layer is positioned at said long convex area.

9. The interlabial pad according to claim 1, wherein a miniature sheet piece is attached to said back face side sheet.

10. The interlabial pad according to claim 3, wherein the diffusion layer comprises a fiber material made into a sheet.

11. The interlabial pad according to claim 10, wherein the diffusion layer provides an area for diffusion of body fluid in the longitudinal direction.

12. The interlabial pad according to claim 10, wherein the diffusion layer includes chemical fibers with a fiber length of 25 to 51 mm.

13. The interlabial pad according to claim 2, wherein the dimension of the diffusion layer in the longitudinal direction is larger than that of the body fluid storage layer.

14. The interlabial pad according to claim 7, wherein
the diffusion layer comprises a third fibrous assembly;
the third fibrous assembly comprises third fibers; and
the third fibers are longer than the second fibers.

15. An interlabial pad comprising:
an absorbent body having a body fluid storage layer, a labial-following layer, and a diffusion layer positioned between the labial-following layer and the body fluid storage layer;
a covering material having a water-permeable surface side sheet, for facing the labia of a wearer, and a back face side sheet, for facing the body fluid storage layer; and
a side end portion, joining the surface side sheet with the back face side sheet,
wherein at least a part of the labial-following layer is positioned between the surface side sheet and the diffusion layer, and the labial-following layer is adapted to deform together with the covering material in accordance with a labia shape of the wearer;
the body fluid storage layer is in contact with the diffusion layer, and the diffusion layer is in contact with the labial-following layer to allow movement of body fluid from the labial-following layer to the body fluid storage layer;
spaces are formed at both sides of the body fluid storage layer between the body fluid storage layer and the surface side sheet of the covering material, at least one of the spaces becoming smaller when the interlabial pad is folded in two along a folding axis so that the back face side sheet overlaps itself; and
the labial-following layer is more flexible than the body fluid storage layer, wherein the garment side of the body fluid storage layer is covered with tissue having 10 to 20 $g/m^2$ specific weight per unit;
a pulp selected from a range of fiber length of 1 to 10 mm is laminated at 60 to 120 $g/m^2$ by specific weight per unit in the body fluid storage layer on an upper face thereof;
a mesh spun lace of rayon with a fiber length of 25 to 51 mm is laid down in the diffusion layer at a body side of the body fluid storage layer; and
a mixture at a mixing ratio of 60 to 90% rayon selected from a range of a fiber length of 20 to 51 mm and 40 to 10% of natural cotton is laminated at 150 to 250 $g/m^2$ by specific weight per unit in the labial-following layer on an upper face thereof.

* * * * *